(12) United States Patent
Yu et al.

(10) Patent No.: US 9,309,541 B2
(45) Date of Patent: Apr. 12, 2016

(54) BIOLOGICAL PRODUCTION OF ORGANIC COMPOUNDS

(71) Applicants: Jianping Yu, Golden, CO (US); Troy Paddock, Wheat Ridge, CO (US); Damian Carrieri, Denver, CO (US); Pin-Ching Maness, Golden, CO (US); Michael Seibert, Lakewood, CO (US)

(72) Inventors: Jianping Yu, Golden, CO (US); Troy Paddock, Wheat Ridge, CO (US); Damian Carrieri, Denver, CO (US); Pin-Ching Maness, Golden, CO (US); Michael Seibert, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 14/643,788

(22) Filed: Mar. 10, 2015

(65) Prior Publication Data

US 2015/0247170 A1 Sep. 3, 2015

Related U.S. Application Data

(63) Continuation of application No. 13/560,580, filed on Jul. 27, 2012, now abandoned.

(60) Provisional application No. 61/512,075, filed on Jul. 27, 2011.

(51) Int. Cl.
*C12P 5/02* (2006.01)
*C12P 7/50* (2006.01)
*C12P 7/40* (2006.01)
*C12N 9/02* (2006.01)
*C12N 15/63* (2006.01)
(Continued)

(52) U.S. Cl.
CPC ... *C12P 7/50* (2013.01); *C12N 1/12* (2013.01); *C12N 9/0069* (2013.01); *C12N 15/63* (2013.01); *C12P 5/026* (2013.01); *C12P 7/40* (2013.01); *C12R 1/01* (2013.01)

(58) Field of Classification Search
None
See application file for complete search history.

(56) References Cited

U.S. PATENT DOCUMENTS 4,952,501 A 8/1990 Jasin et al.
5,536,659 A * 7/1996 Fukuda ................... C12P 5/026
                                                        435/252.33
(Continued)

FOREIGN PATENT DOCUMENTS

WO   WO 2009078712 A2 *  6/2009 ............... C12N 1/20
WO      2009/105714        8/2009
(Continued)

OTHER PUBLICATIONS

Carrieri et al., "Photo-catalytic Conversion of Carbon Dioxide to Organic Acids by a Recombinant Cyanobacterium Incapable of Glycogen Storage", Energy & Environmental Science, 2012, vol. 5, pp. 9457-9461.
(Continued)

*Primary Examiner* — Robert Mondesi
*Assistant Examiner* — Richard Ekstrom
(74) *Attorney, Agent, or Firm* — John C. Stolpa

(57) ABSTRACT

Strains of cyanobacteria that produce high levels of alpha ketoglutarate (AKG) and pyruvate are disclosed herein. Methods of culturing these cyanobacteria to produce AKG or pyruvate and recover AKG or pyruvate from the culture are also described herein. Nucleic acid sequences encoding polypeptides that function as ethylene-forming enzymes and their use in the production of ethylene are further disclosed herein. These nucleic acids may be expressed in hosts such as cyanobacteria, which in turn may be cultured to produce ethylene.

19 Claims, 28 Drawing Sheets

(51) Int. Cl.
  *C12R 1/01* (2006.01)
  *C12N 1/12* (2006.01)

(56) References Cited

U.S. PATENT DOCUMENTS

| | | | |
|---|---|---|---|
| 7,968,321 | B1 | 6/2011 | Green et al. |
| 7,981,647 | B2 | 7/2011 | Berry et al. |
| 8,048,666 | B1 | 11/2011 | Green et al. |
| 8,163,516 | B2 | 4/2012 | Dehring et al. |
| 8,216,816 | B2 | 7/2012 | Green et al. |
| 8,227,237 | B2 | 7/2012 | Reppas et al. |
| 8,465,954 | B2 | 6/2013 | Green et al. |
| 2010/0068776 | A1 | 3/2010 | Woods et al. |
| 2010/0184169 | A1 | 7/2010 | Roberts et al. |
| 2010/0297736 | A1 | 11/2010 | Duhring et al. |
| 2010/0317073 | A1 | 12/2010 | Sayre et al. |
| 2010/0330639 | A1 | 12/2010 | Lee |
| 2011/0008861 | A1* | 1/2011 | Berry ............... C12N 1/20 435/161 |
| 2011/0250659 | A1 | 10/2011 | Roberts et al. |
| 2012/0122193 | A1 | 5/2012 | Berry et al. |
| 2012/0156717 | A1 | 6/2012 | Allnutt et al. |
| 2012/0276637 | A1 | 11/2012 | Zhou et al. |
| 2013/0122553 | A1 | 5/2013 | Maertens et al. |
| 2013/0203136 | A1 | 8/2013 | Yu et al. |

FOREIGN PATENT DOCUMENTS

| | | |
|---|---|---|
| WO | 2009/105733 | 8/2009 |
| WO | 2009/111513 | 9/2009 |
| WO | WO 2010006312 A2 * | 1/2010 ............... C12N 1/20 |
| WO | 2010/044960 | 4/2010 |
| WO | 2012/015949 | 2/2012 |

OTHER PUBLICATIONS

Ernst et al., "Glycogen content and nitrogenase activity in Anabaena variabilis", Archives of Microbiology, 1984, vol. 140, Nos. 2-3, pp. 120-125.

Fukuda et al., "Heterologous expression of the gene for the ethylene-forming enzyme from Pseudomonas syringae in the cyanobacterium Synechococcus", Biotechnology Letters, 1994, vol. 16, No. 1, pp. 1-6.

Miao et al., "Changes in Photosynthesis and Pigmentation in an agp Deletion Mutant of the cyanobacterium *Synechocystis* sp.", Biotechnology Letters, 2003, vol. 25, pp. 391-396.

Miao et al., "Sucrose accumulation in salt-stressed cells of agp gene deletion-mutant in cyanobacterium *Synechocystis* sp. PCC 6803", FEMS Microbiology Letters, 2003, vol. 218, pp. 71-77.

Sakai et al., "Photosynthetic conversion of carbon dioxide to ethylene by the recombinant cyanobacterium, *Synechococcus* sp. PCC 7942, which harbors a gene for the ethylene-forming enzyme of Pseudomonas syringae", Journal of Fermentation and Bioengineering, 1997, vol. 84, No. 5, pp. 434-443.

Suzuki et al., "Carbohydrate Metabolism in Mutants of the Cyanobacterium Synechococcus elongatus PCC 7942 Defective in Glycogen Synthesis", Applied and Environmental Microbiology, May 2010, vol. 76, No. 10, pp. 3153-3159.

Takahama et al., "Construction and analysis of a recombinant cyanobacterium expressing a chromosomally inserted gene for an ethylene-forming enzyme at the psbAI locus", Journal of Bioscience and Bioengineering, 2003, vol. 95, pp. 302-305.

Wu et al., "Modification of Carbon Partitioning to Enhance PHB Production in *Synechocystis* sp. PCC6803", Enzyme and Microbial Technology, 2002, vol. 30, pp. 710-715.

Zang et al., "Optimum conditions for transformation of *Synechocystis* sp. PCC 6803", The Journal of Microbiology, Jun. 2007, vol. 45, No. 3, pp. 241-245.

* cited by examiner

Figure 2
A.
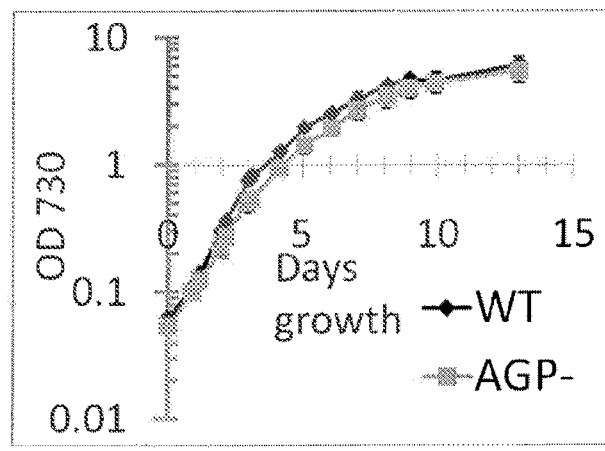
B.
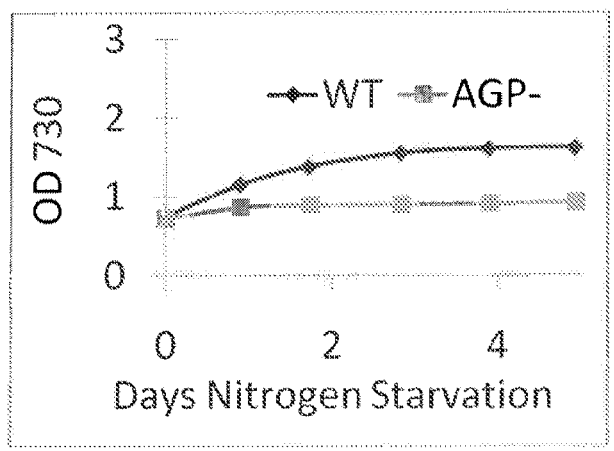
C.
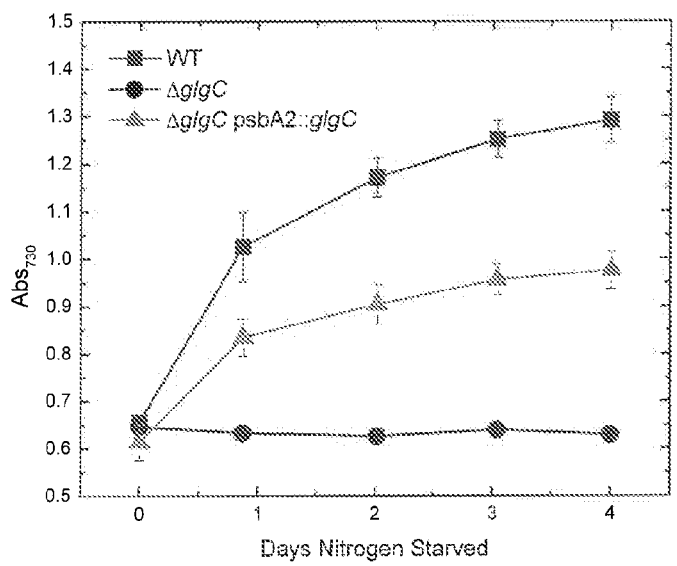

Figure 5
A.
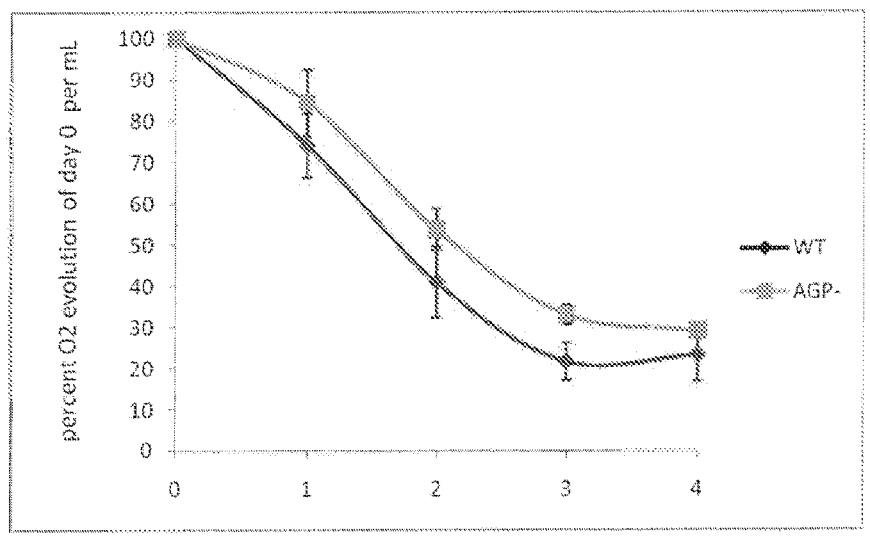
B.
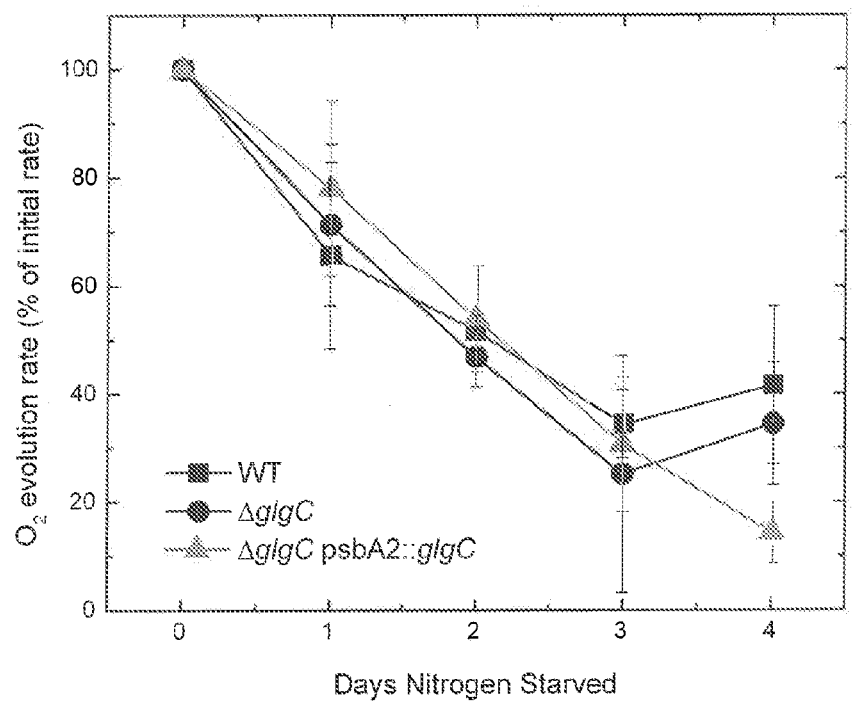
Days Nitrogen Starved

Figure 6
A.
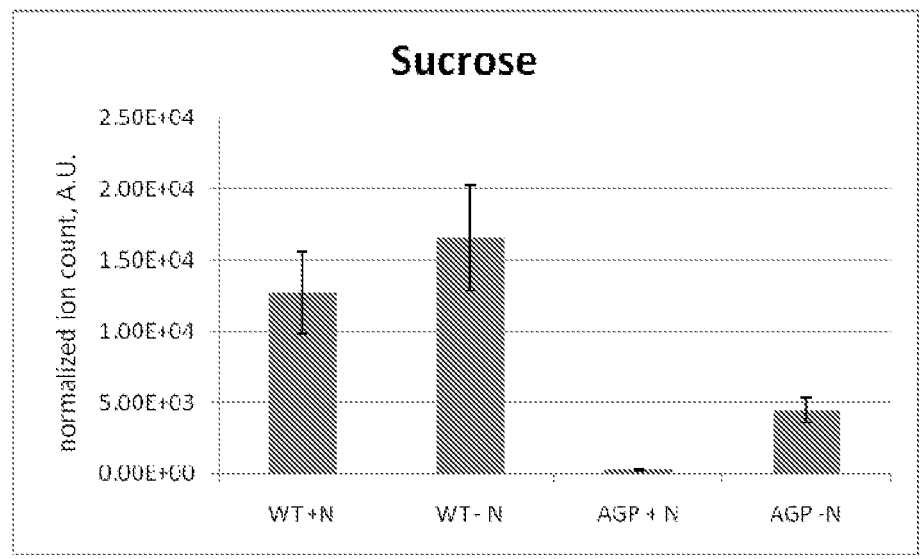
B.
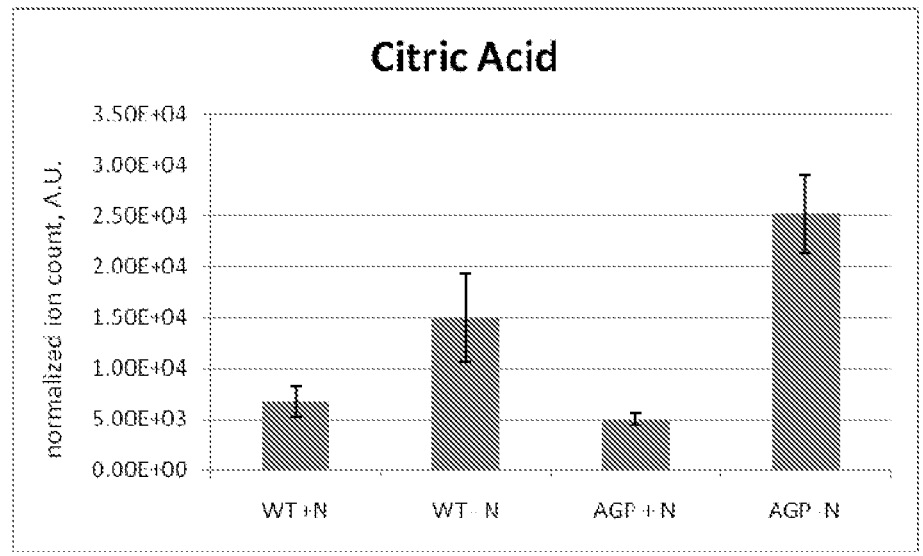

Figure 6
C.
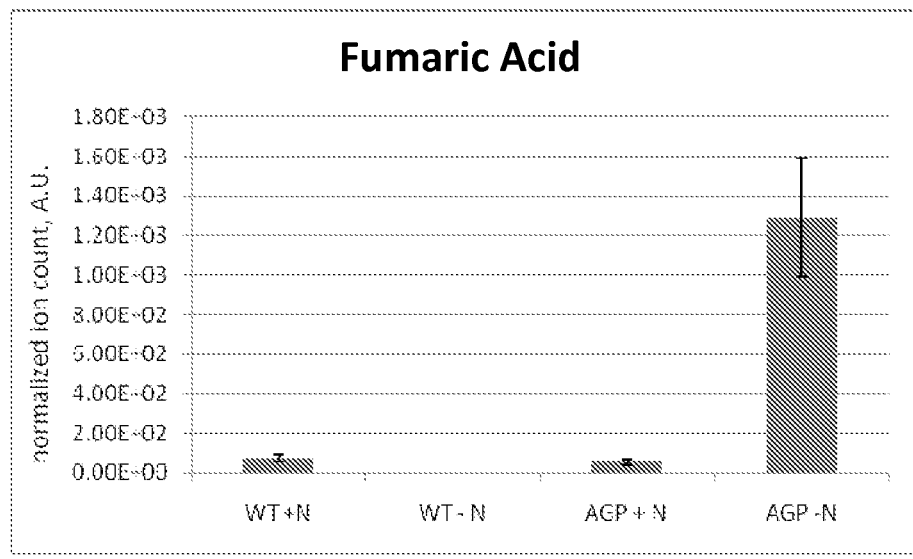
D.
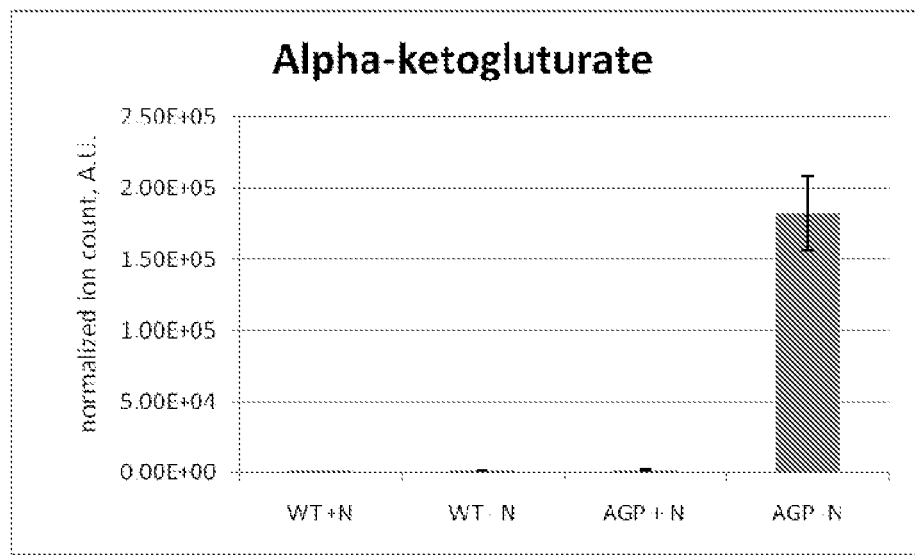

Figure 7
A.
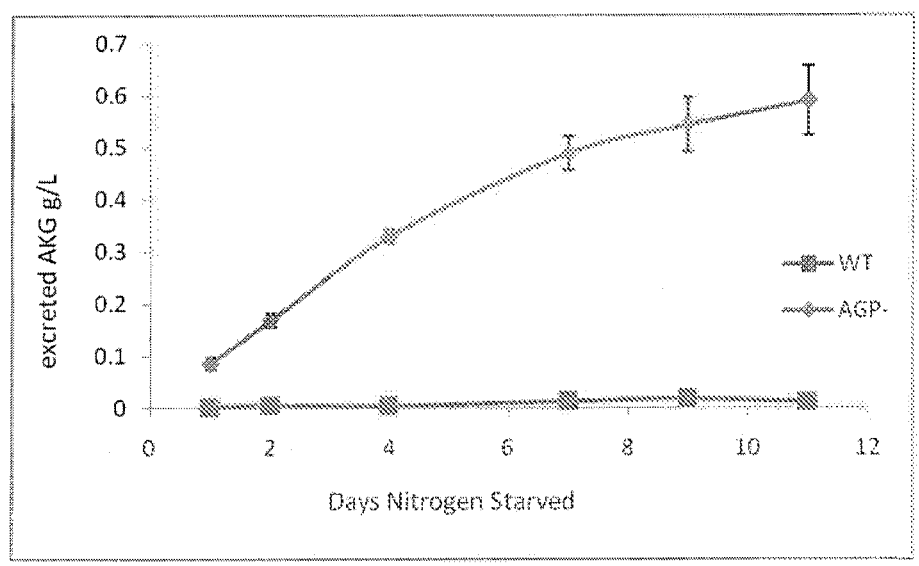
B.
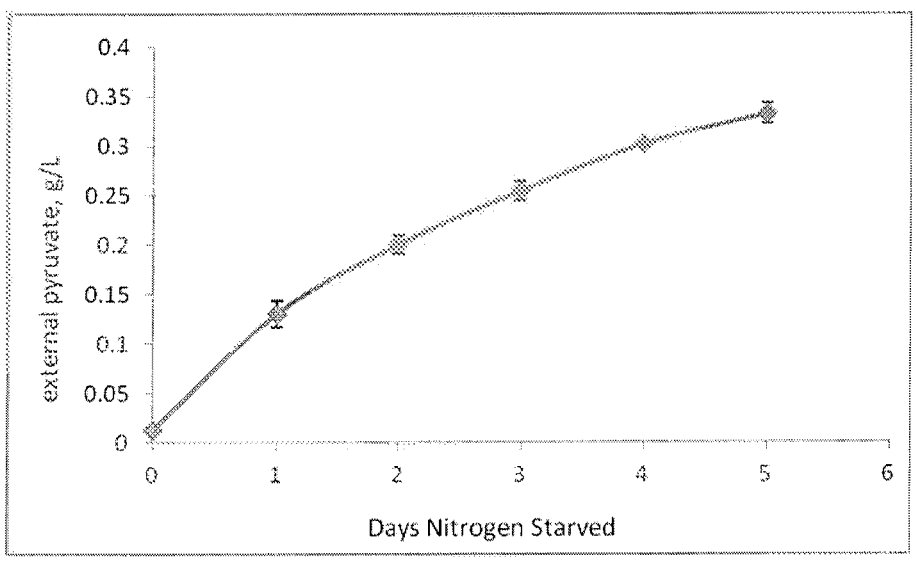

```
GTGTGTTGTTGGCAATCGAGAGGTCTGCTTGTGAAACGTGTCTTAGCGATTATCCTGGGCGGTGGGGCCG
GGACCCGCCTCTATCCTTTAACCAAACTCAGAGCCAAACCCGCAGTTCCCTTGGCCGGAAAGTATCGCCT
CATCGATATTCCCGTCAGTAATTGCATCAACTCAGAAATCGTTAAAATTTACGTCCTTACCCAGTTTAAT
TCCGCCTCCCTTAACCGTCACATCAGCCGGGCCTATAATTTTTCCGGCTTCCAAGAAGGATTTGTGGAAG
TCCTCGCCGCCCAACAAACCAAAGATAATCCTGATTGGTTTCAGGGCACTGCTGATGCGGTACGGCAATA
CCTCTGGTTGTTTAGGGAATGGGACGTAGATGAATATCTTATTCTGTCCGGCGACCATCTCTACCGCATG
GATTACGCCCAATTTGTTAAAAGACACCGGGAAACCAATGCCGACATAACCCTTTCCGTTGTGCCCGTGG
ATGACAGAAAGGCACCCGAGCTGGGCTTAATGAAAATCGACGCCCAGGGCAGAATTACTGACTTTTCTGA
AAAGCCCCAGGGGGAAGCCCTCCGGGCCATGCAGGTGGACACCAGCGTTTTGGGCCTAAGTGCGGAGAAG
GCTAAGCTTAATCCTTACATTGCCTCCATGGGCATTTACGTTTTCAAGAAGGAAGTATTGCACAACCTCC
TGGAAAAATATGAAGGGGCAACGGACTTTGGCAAAGAAATCATTCCTGATTCAGCCAGTGATCACAATCT
GCAAGCCTATCTCTTTGATGACTATTGGGAAGACATTGGTACCATTGAAGCCTTCTATGAGGCTAATTTA
GCCCTGACCAAACAACCTAGTCCCGACTTTAGTTTTTATAACGAAAAAGCCCCCATCTATACCAGGGGTC
GTTATCTTCCCCCCACCAAAATGTTGAATTCCACCGTGACGGAATCCATGATCGGGGAAGGTTGCATGAT
TAAGCAATGTCGCATCCACCACTCAGTTTTAGGCATTCGCAGTCGCATTGAATCTGATTGCACCATTGAG
GATACTTTGGTGATGGGCAATGATTTCTACGAATCTTCATCAGAACGAGACACCCTCAAAGCCCGGGGGG
AAATTGCCGCTGGCATAGGTTCCGGCACCACTATCCGCCGAGCCATCATCGACAAAAATGCCCGCATCGG
CAAAAACGTCATGATTGTCAACAAGGAAATGTCCAGGAGGCTAACCGGGAAGAGTTAGGTTTTTACATC
CGCAATGGCATCGTAGTAGTGATTAAAAATGTCACGATCGCCGACGGCACGGTAATCTAG
```

B.

```
  1 mccwqsrgll vkrvlaiilg ggagtrlypl tklrakpavp lagkyrlidi pvsncinsei
 61 vkiyvltqfn saslnrhisr aynfsgfqeg fvevlaaqqt kdnpdwfqgt adavrqylwl
121 frewdvdeyl ilsgdhlyrm dyaqfvkrhr etnaditlsv vpvddrkape lglmkidaqg
181 ritdfsekpq gealramqvd tsvlglsaek aklnpyiasm giyvfkkevl hnllekyega
241 tdfgkeiipd sasdhnlqay lfddywedig tieafyeanl altkqpspdf sfynekapiy
301 trgrylpptk mlnstvtesm igegcmikqc rihhsvlgir sriesdctie dtlvmgndfy
361 essserdtlk argeiaagig sgttirraii dknarigknv mivnkenvqe anreelgfyi
421 rngivvvikn vtiadgtvi
```

Figure 12
A.
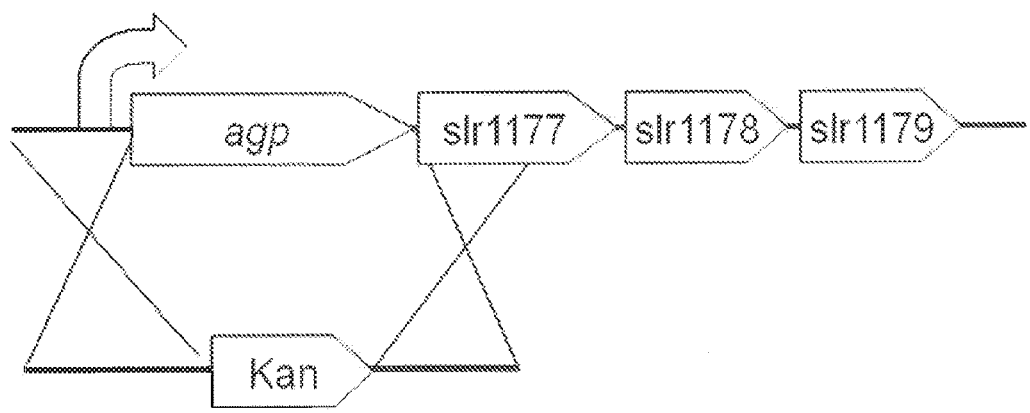
B.
First Round PCR:
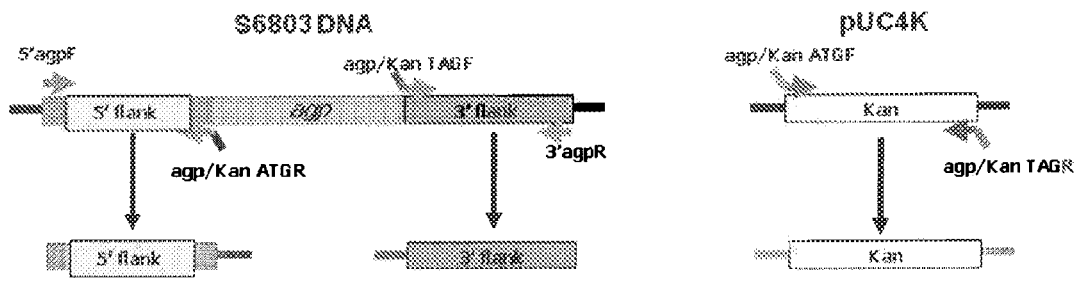
Second Round PCR:
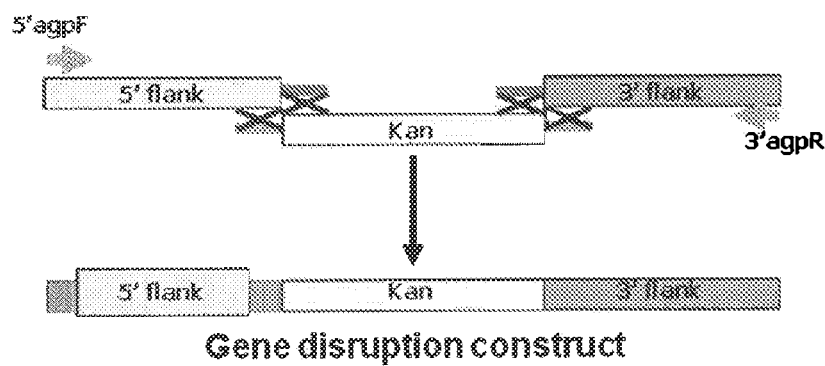
Gene disruption construct

A.

Figure 16
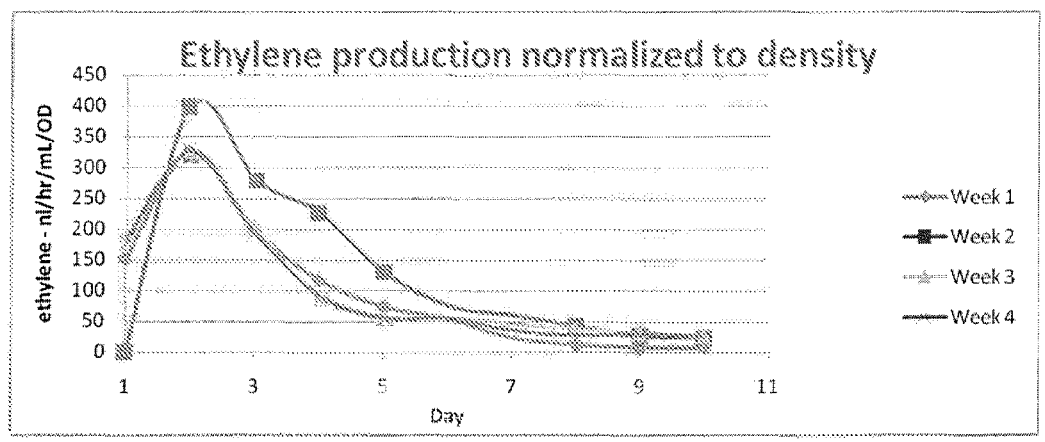
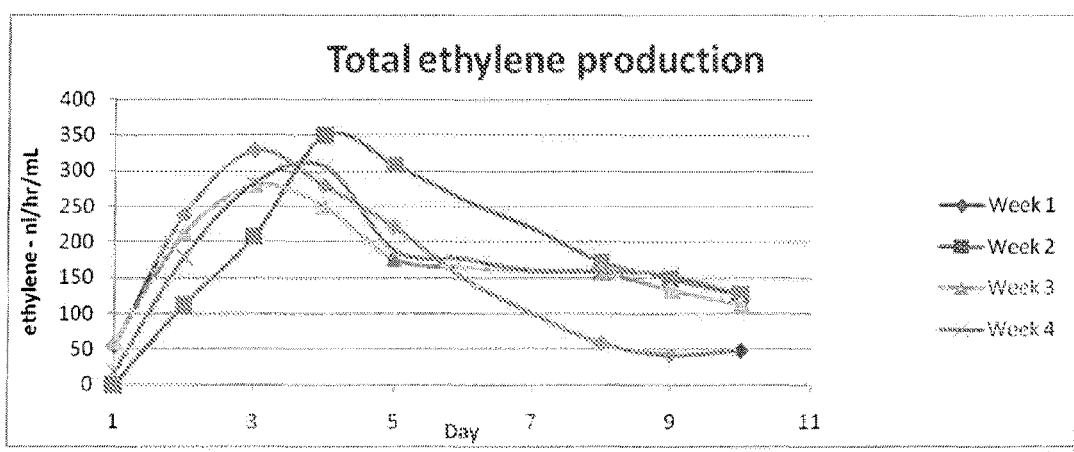

Figure 17
A.
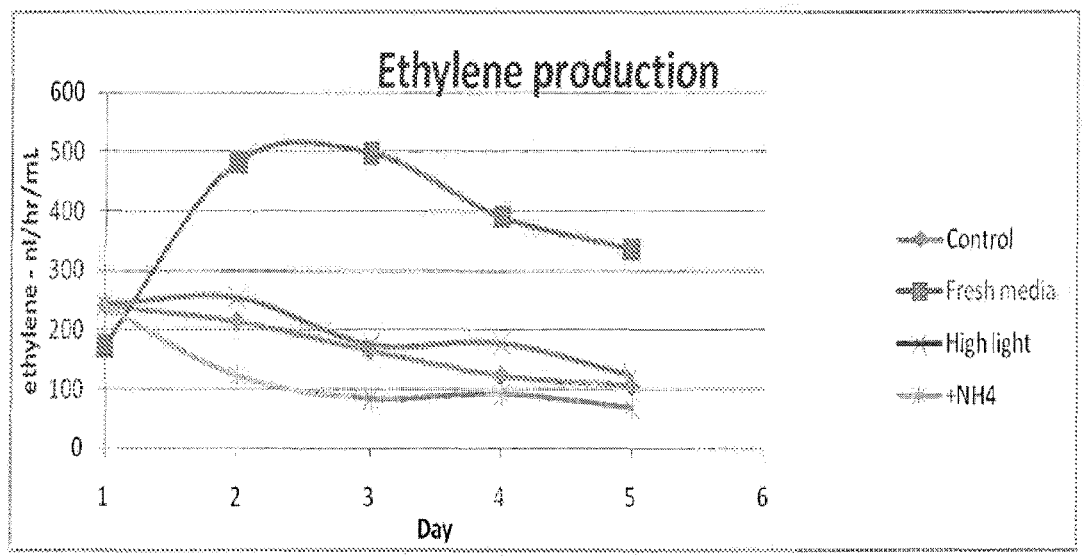
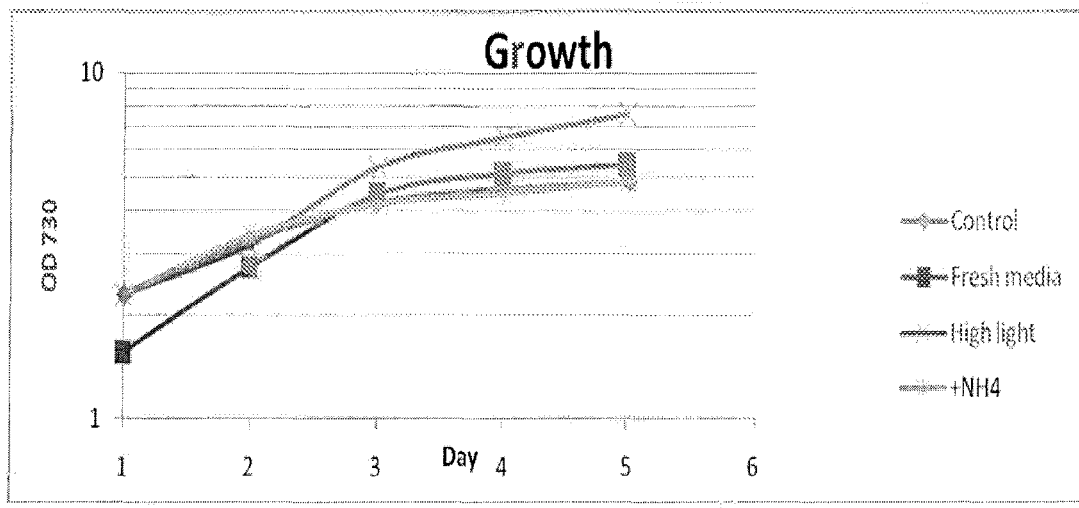

Figure 17
B.
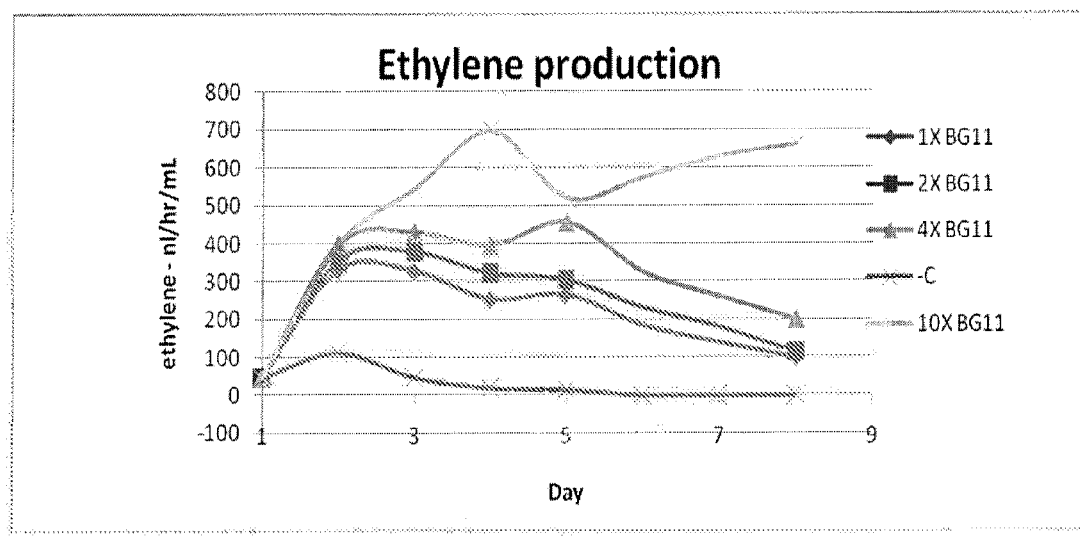
C.
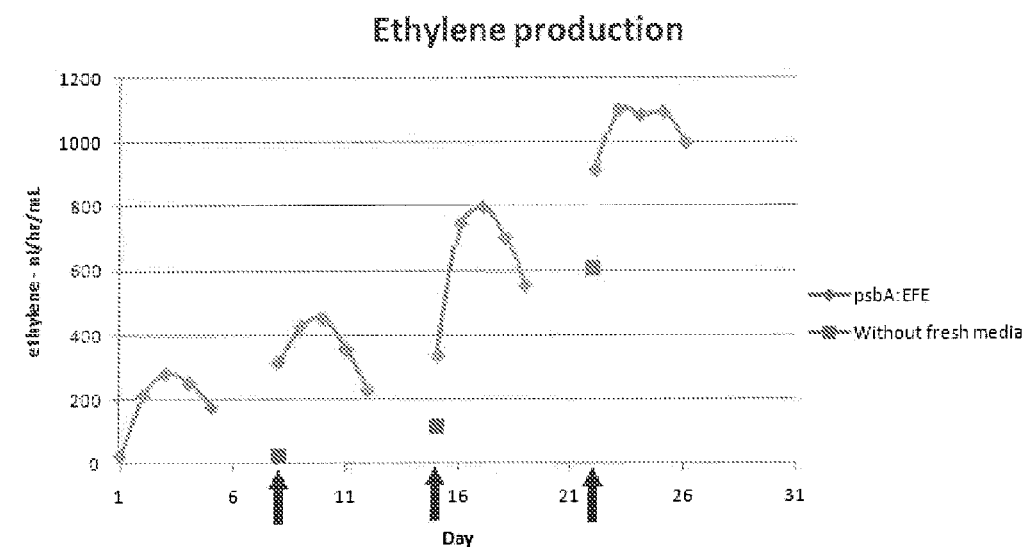

Figure 18
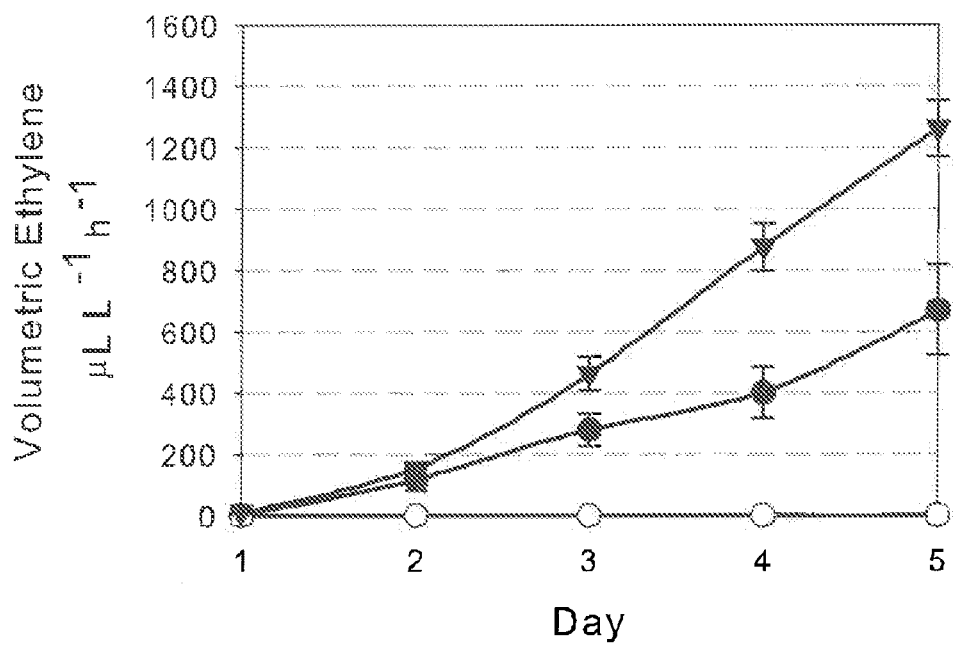
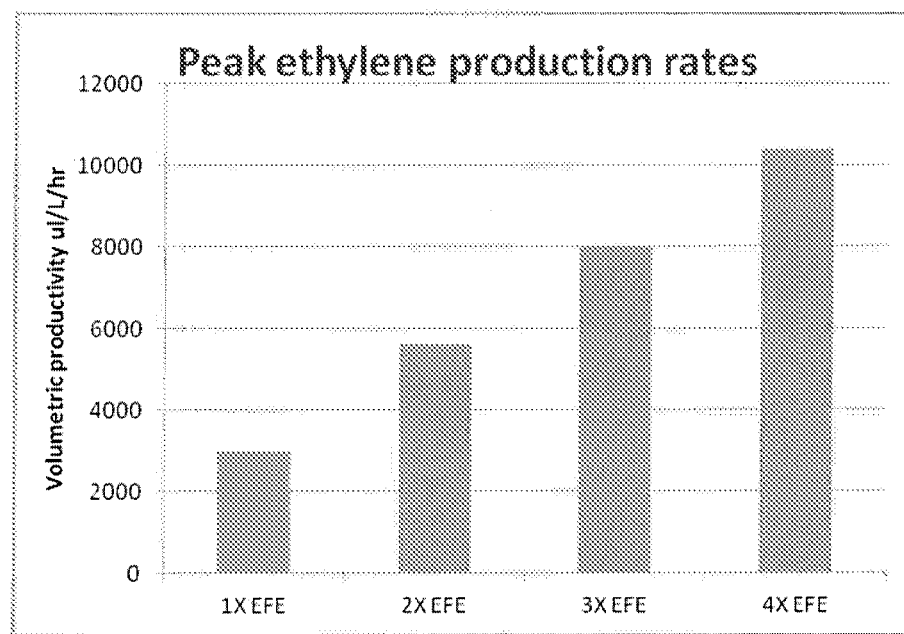

Figure 19
A.
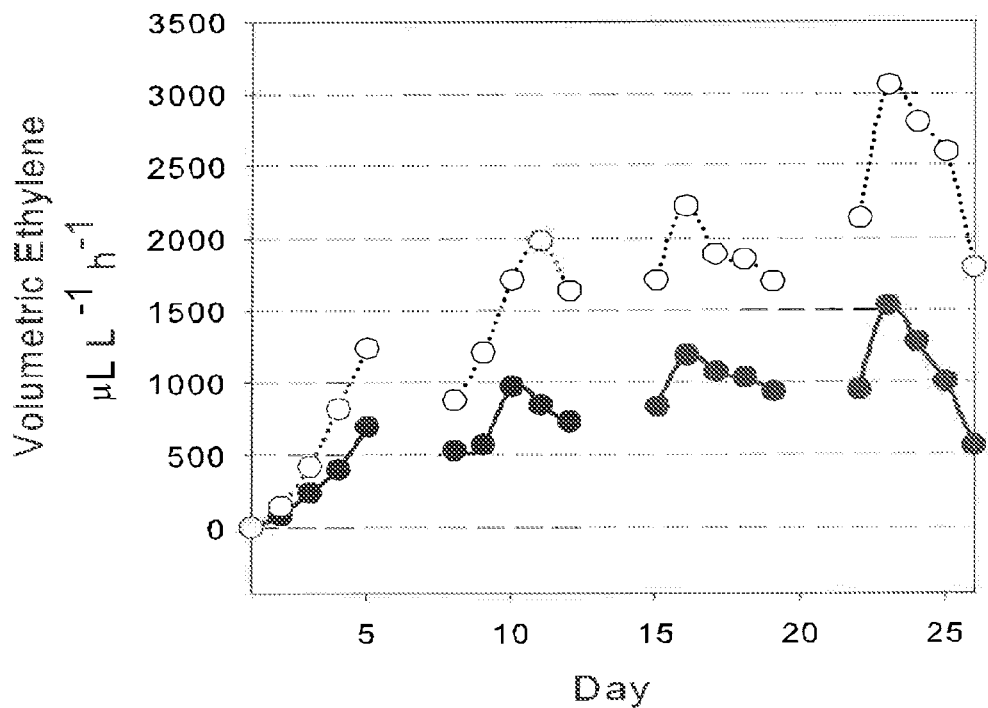
B.
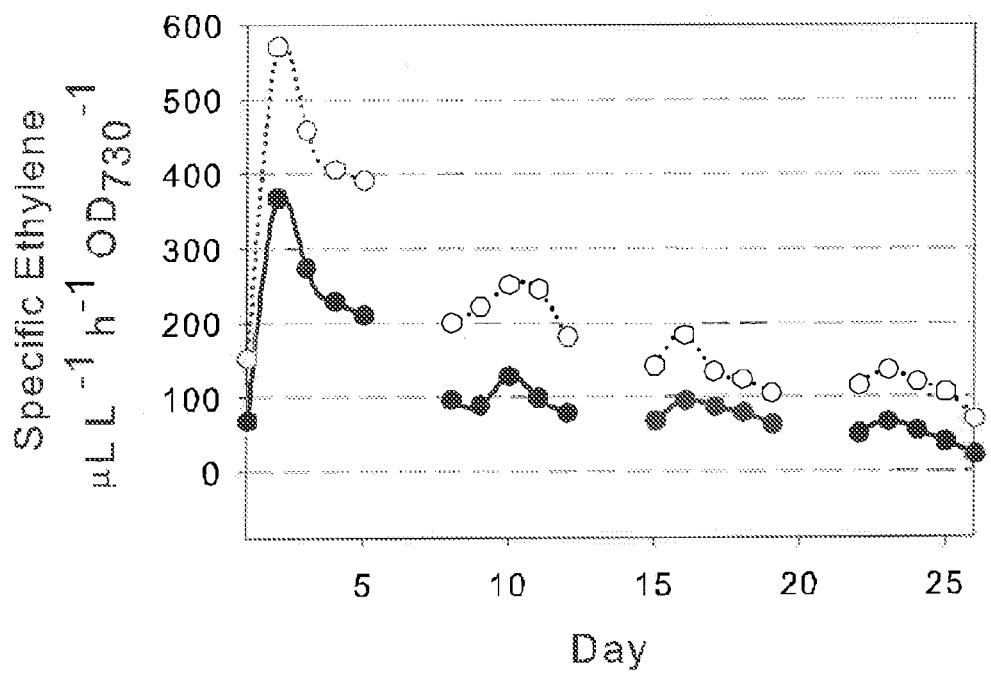

Figure 19
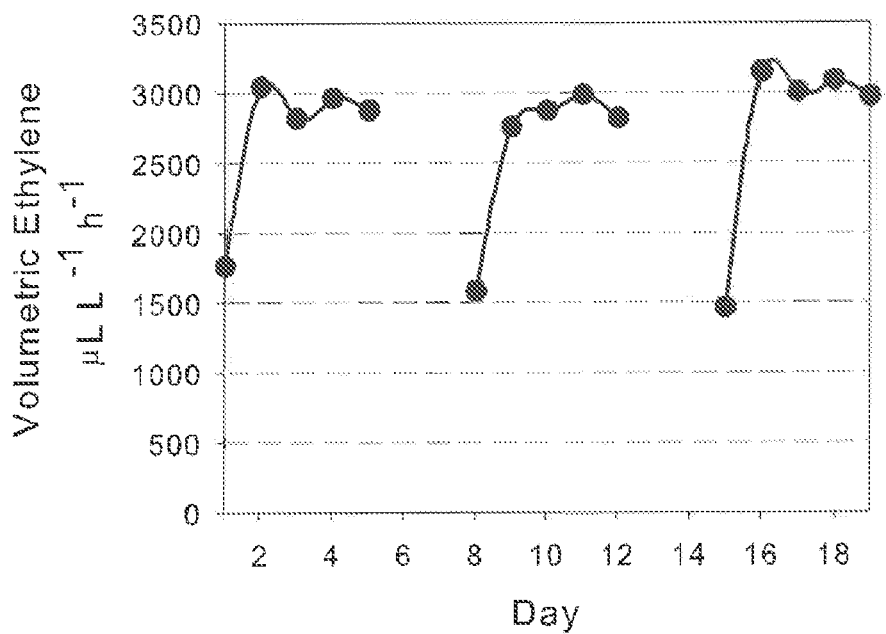
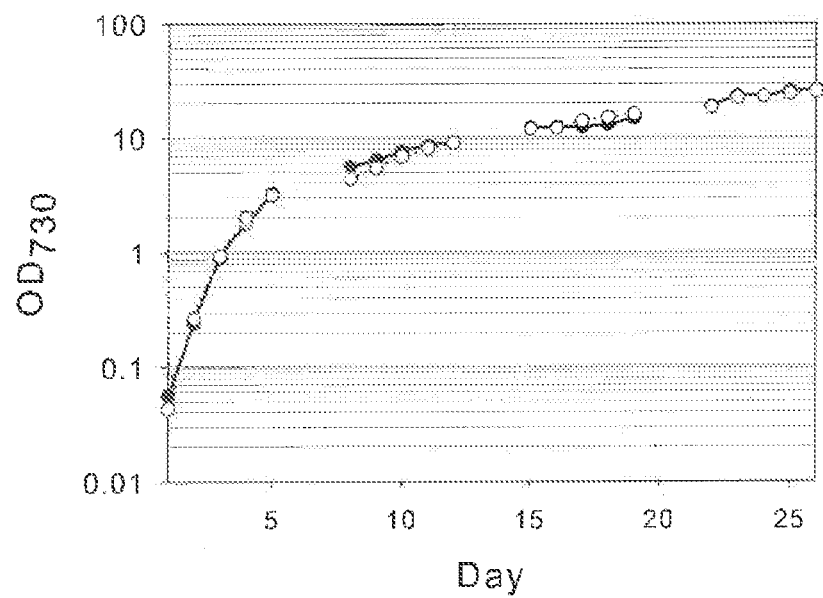

Figure 20
A.
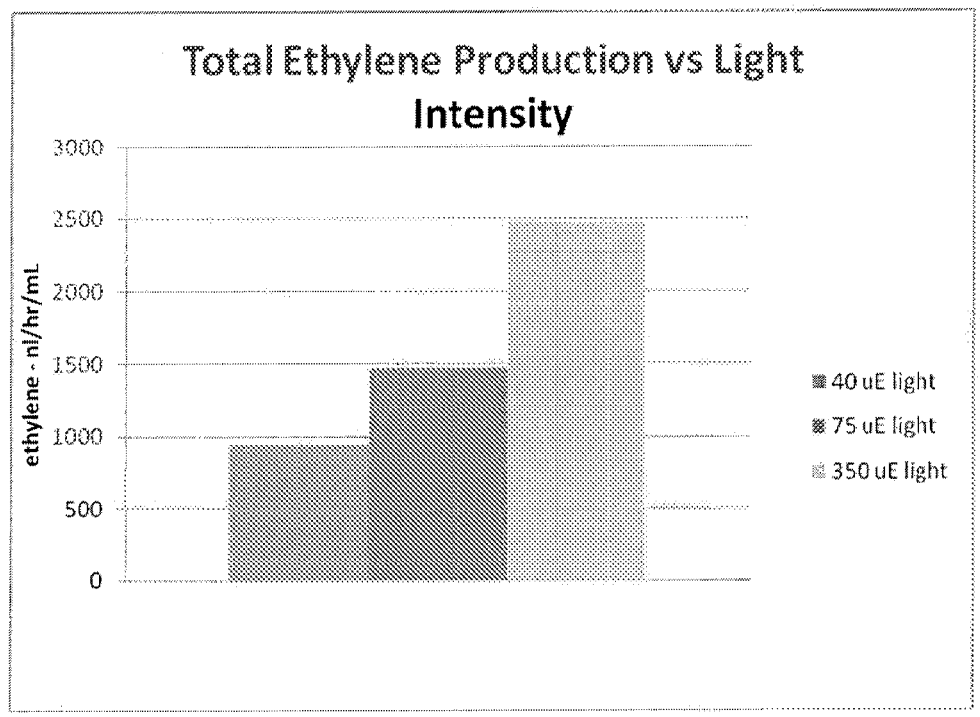
B.
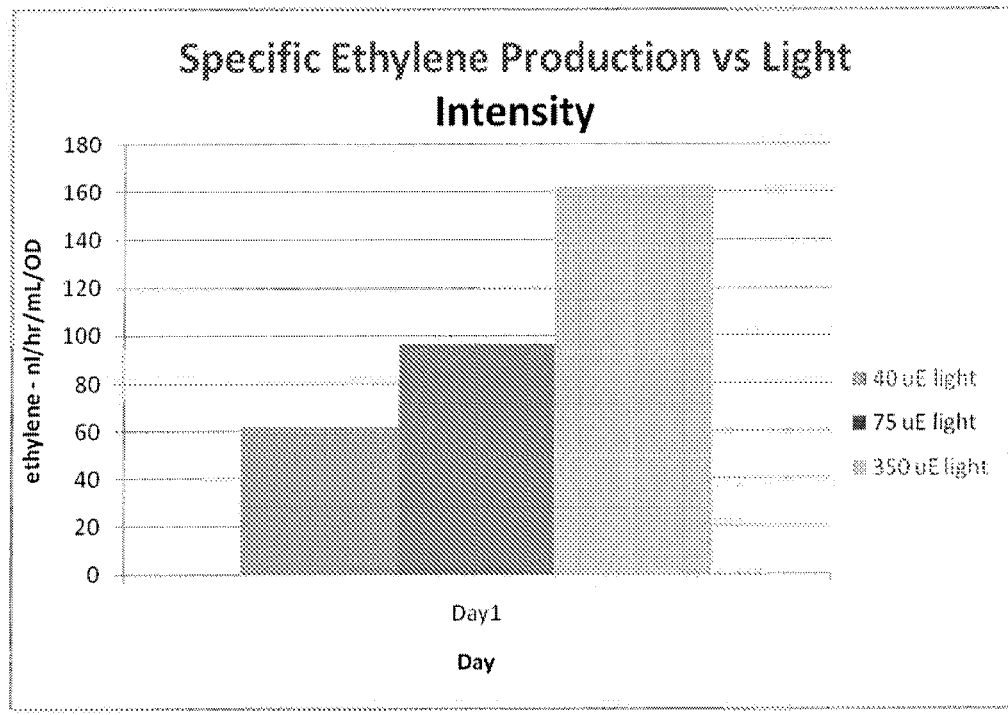

Figure 21
A.
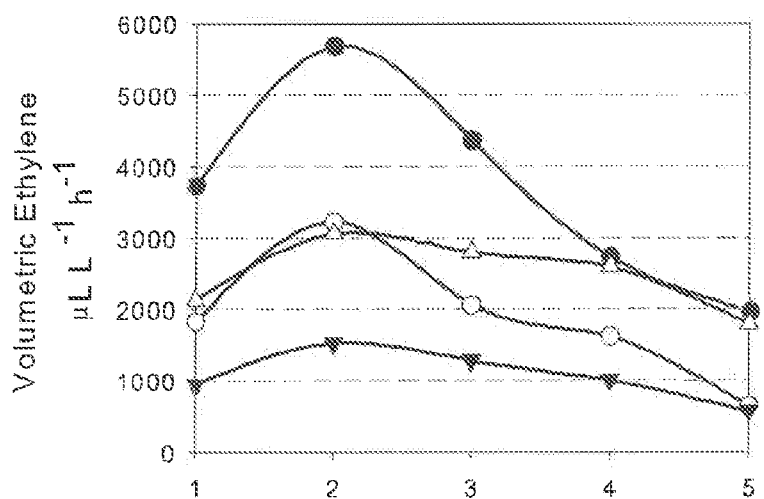
B.
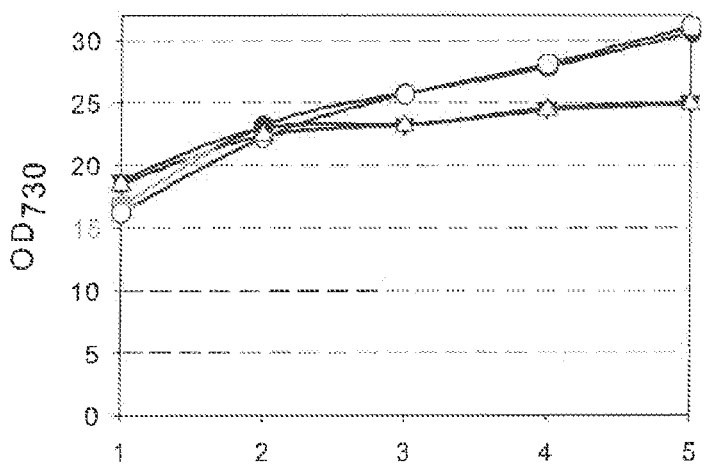
C.
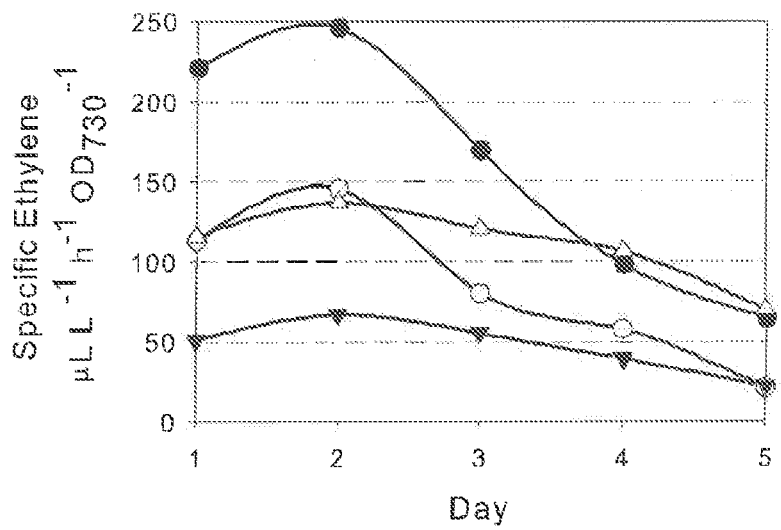

Figure 22

ATGACCAATTTGCAAACTTTTGAATTACCCACCGAAGTGACTGGCTGTGCCGCTGATATTTCCTTAGG
TCGCGCCCTGATTCAAGCCTGGCAGAAAGACGGCATTTTTCAAATTAAAACCGATAGTGAACAAGAC
CGTAAAACTCAAGAAGCTATGGCCGCTAGCAAACAGTTTTGTAAAGAACCCTTGACCTTTAAATCCA
GTTGCGTGAGCGATTTAACTTATTCTGGCTACGTGGCCTCCGGTGAAGAAGTTACCGCTGGGAAACC
CGACTTTCCCGAAATTTTTACCGTGTGTAAAGATTTATCCGTGGGCGACCAACGGGTTAAAGCTGGA
TGGCCCTGTCATGGCCCCGTTCCCTGGCCCAACAACACCTACCAGAAAAGTATGAAAACTTTTATGG
AAGAATTGGGGTTAGCCGGAGAACGCTTGTTAAAACTGACCGCTTTGGGGTTTGAACTGCCCATTAA
TACCTTTACTGATTTGACCCGTGACGGATGGCATCACATGCGCGTGTTACGTTTTCCCCCCCAAACCT
CCACTCTGAGTCGGGGCATTGGTGCCCATACCGATTATGGTCTGTTGGTGATTGCCGCTCAGGATGA
CGTTGGCGGTCTGTACATTCGTCCCCCCGTGGAAGGGGAAAAACGGAATCGCAACTGGTTGCCCGG
CGAAAGCTCTGCCGGCATGTTTGAACATGACGAACCCTGGACCTTTGTTACCCCCACTCCCGGGGTG
TGGACCGTTTTTCCCGGAGATATTCTGCAATTTATGACCGGGGGACAGTTACTGTCCACTCCCCATAA
AGTGAAATTGAATACCCGTGAACGGTTTGCCTGTGCTTATTTTCACGAACCCAACTTTGAAGCCTCTG
CTTACCCCTTGTTTGAACCCTCCGCCAATGAACGGATTCATTATGGCGAACACTTTACCAACATGTTT
ATGCGGTGCTACCCCGATCGCATTACCACTCAACGTATTAACAAAGAAAACCGGTTAGCCCATCTGG
AAGATTTGAAAAAATACAGTGACACCCGCGCTACTGGTAGC

Figure 23

MTNLQTFELP TEVTGCAADI SLGRALIQAW QKDGIFQIKT DSEQDRKTQE AMAASKQFCK

EPLTFKSSCV SDLTYSGYVA SGEEVTAGKP DFPEIFTVCK DLSVGDQRVK AGWPCHGPVP

WPNNTYQKSM KTFMEELGLA GERLLKLTAL GFELPINTFT DLTRDGWHHM RVLRFPPQTS

TLSRGIGAHT DYGLLVIAAQ DDVGGLYIRP PVEGEKRNRN WLPGESSAGM FEHDEPWTFV

TPTPGVWTVF PGDILQFMTG GQLLSTPHKV KLNTRERFAC AYFHEPNFEA SAYPLFEPSA

NERIHYGEHF TNMFMRCYPD RITTQRINKE NRLAHLEDLK KYSDTRATGS

SEQUENCE LISTING

```
<160> NUMBER OF SEQ ID NOS: 14

<210> SEQ ID NO 1
<211> LENGTH: 1320
<212> TYPE: DNA
<213> ORGANISM: Synechocystis sp. PCC 6803
```

<220> FEATURE:
<221> NAME/KEY: CDS
<222> LOCATION: (1)..(1320)

<400> SEQUENCE: 1

| | | | | | | | | | | | | | | | | |
|---|---|---|---|---|---|---|---|---|---|---|---|---|---|---|---|---|
| gtg | tgt | tgt | tgg | caa | tcg | aga | ggt | ctg | ctt | gtg | aaa | cgt | gtc | tta | gcg | 48 |
| Val | Cys | Cys | Trp | Gln | Ser | Arg | Gly | Leu | Leu | Val | Lys | Arg | Val | Leu | Ala | |
| 1 | | | | 5 | | | | | 10 | | | | | 15 | | |
| att | atc | ctg | ggc | ggt | ggg | gcc | ggg | acc | cgc | ctc | tat | cct | tta | acc | aaa | 96 |
| Ile | Ile | Leu | Gly | Gly | Gly | Ala | Gly | Thr | Arg | Leu | Tyr | Pro | Leu | Thr | Lys | |
| | | | 20 | | | | | 25 | | | | | 30 | | | |
| ctc | aga | gcc | aaa | ccc | gca | gtt | ccc | ttg | gcc | gga | aag | tat | cgc | ctc | atc | 144 |
| Leu | Arg | Ala | Lys | Pro | Ala | Val | Pro | Leu | Ala | Gly | Lys | Tyr | Arg | Leu | Ile | |
| | 35 | | | | | 40 | | | | | 45 | | | | | |
| gat | att | ccc | gtc | agt | aat | tgc | atc | aac | tca | gaa | atc | gtt | aaa | att | tac | 192 |
| Asp | Ile | Pro | Val | Ser | Asn | Cys | Ile | Asn | Ser | Glu | Ile | Val | Lys | Ile | Tyr | |
| 50 | | | | | 55 | | | | | 60 | | | | | | |
| gtc | ctt | acc | cag | ttt | aat | tcc | gcc | tcc | ctt | aac | cgt | cac | atc | agc | cgg | 240 |
| Val | Leu | Thr | Gln | Phe | Asn | Ser | Ala | Ser | Leu | Asn | Arg | His | Ile | Ser | Arg | |
| 65 | | | | | 70 | | | | | 75 | | | | | 80 | |
| gcc | tat | aat | ttt | tcc | ggc | ttc | caa | gaa | gga | ttt | gtg | gaa | gtc | ctc | gcc | 288 |
| Ala | Tyr | Asn | Phe | Ser | Gly | Phe | Gln | Glu | Gly | Phe | Val | Glu | Val | Leu | Ala | |
| | | | | 85 | | | | | 90 | | | | | 95 | | |
| gcc | caa | caa | acc | aaa | gat | aat | cct | gat | tgg | ttt | cag | ggc | act | gct | gat | 336 |
| Ala | Gln | Gln | Thr | Lys | Asp | Asn | Pro | Asp | Trp | Phe | Gln | Gly | Thr | Ala | Asp | |
| | | | 100 | | | | | 105 | | | | | 110 | | | |
| gcg | gta | cgg | caa | tac | ctc | tgg | ttg | ttt | agg | gaa | tgg | gac | gta | gat | gaa | 384 |
| Ala | Val | Arg | Gln | Tyr | Leu | Trp | Leu | Phe | Arg | Glu | Trp | Asp | Val | Asp | Glu | |
| | 115 | | | | | 120 | | | | | 125 | | | | | |
| tat | ctt | att | ctg | tcc | ggc | gac | cat | ctc | tac | cgc | atg | gat | tac | gcc | caa | 432 |
| Tyr | Leu | Ile | Leu | Ser | Gly | Asp | His | Leu | Tyr | Arg | Met | Asp | Tyr | Ala | Gln | |
| 130 | | | | | 135 | | | | | 140 | | | | | | |
| ttt | gtt | aaa | aga | cac | cgg | gaa | acc | aat | gcc | gac | ata | acc | ctt | tcc | gtt | 480 |
| Phe | Val | Lys | Arg | His | Arg | Glu | Thr | Asn | Ala | Asp | Ile | Thr | Leu | Ser | Val | |
| 145 | | | | | 150 | | | | | 155 | | | | | 160 | |
| gtg | ccc | gtg | gat | gac | aga | aag | gca | ccc | gag | ctg | ggc | tta | atg | aaa | atc | 528 |
| Val | Pro | Val | Asp | Asp | Arg | Lys | Ala | Pro | Glu | Leu | Gly | Leu | Met | Lys | Ile | |
| | | | | 165 | | | | | 170 | | | | | 175 | | |
| gac | gcc | cag | ggc | aga | att | act | gac | ttt | tct | gaa | aag | ccc | cag | ggg | gaa | 576 |
| Asp | Ala | Gln | Gly | Arg | Ile | Thr | Asp | Phe | Ser | Glu | Lys | Pro | Gln | Gly | Glu | |
| | | | 180 | | | | | 185 | | | | | 190 | | | |
| gcc | ctc | cgg | gcc | atg | cag | gtg | gac | acc | agc | gtt | ttg | ggc | cta | agt | gcg | 624 |
| Ala | Leu | Arg | Ala | Met | Gln | Val | Asp | Thr | Ser | Val | Leu | Gly | Leu | Ser | Ala | |
| | | 195 | | | | | 200 | | | | | 205 | | | | |
| gag | aag | gct | aag | ctt | aat | cct | tac | att | gcc | tcc | atg | ggc | att | tac | gtt | 672 |
| Glu | Lys | Ala | Lys | Leu | Asn | Pro | Tyr | Ile | Ala | Ser | Met | Gly | Ile | Tyr | Val | |
| | 210 | | | | | 215 | | | | | 220 | | | | | |
| ttc | aag | aag | gaa | gta | ttg | cac | aac | ctc | ctg | gaa | aaa | tat | gaa | ggg | gca | 720 |
| Phe | Lys | Lys | Glu | Val | Leu | His | Asn | Leu | Leu | Glu | Lys | Tyr | Glu | Gly | Ala | |
| 225 | | | | | 230 | | | | | 235 | | | | | 240 | |
| acg | gac | ttt | ggc | aaa | gaa | atc | att | cct | gat | tca | gcc | agt | gat | cac | aat | 768 |
| Thr | Asp | Phe | Gly | Lys | Glu | Ile | Ile | Pro | Asp | Ser | Ala | Ser | Asp | His | Asn | |
| | | | | 245 | | | | | 250 | | | | | 255 | | |
| ctg | caa | gcc | tat | ctc | ttt | gat | gac | tat | tgg | gaa | gac | att | ggt | acc | att | 816 |
| Leu | Gln | Ala | Tyr | Leu | Phe | Asp | Asp | Tyr | Trp | Glu | Asp | Ile | Gly | Thr | Ile | |
| | | | 260 | | | | | 265 | | | | | 270 | | | |
| gaa | gcc | ttc | tat | gag | gct | aat | tta | gcc | ctg | acc | aaa | caa | cct | agt | ccc | 864 |
| Glu | Ala | Phe | Tyr | Glu | Ala | Asn | Leu | Ala | Leu | Thr | Lys | Gln | Pro | Ser | Pro | |
| | | 275 | | | | | 280 | | | | | 285 | | | | |
| gac | ttt | agt | ttt | tat | aac | gaa | aaa | gcc | ccc | atc | tat | acc | agg | ggt | cgt | 912 |

```
                    Asp Phe Ser Phe Tyr Asn Glu Lys Ala Pro Ile Tyr Thr Arg Gly Arg
                        290                 295                 300 tat ctt ccc ccc acc aaa atg ttg aat tcc acc gtg acg gaa tcc atg         960
Tyr Leu Pro Pro Thr Lys Met Leu Asn Ser Thr Val Thr Glu Ser Met
305                 310                 315                 320 atc ggg gaa ggt tgc atg att aag caa tgt cgc atc cac cac tca gtt        1008
Ile Gly Glu Gly Cys Met Ile Lys Gln Cys Arg Ile His His Ser Val
                325                 330                 335 tta ggc att cgc agt cgc att gaa tct gat tgc acc att gag gat act        1056
Leu Gly Ile Arg Ser Arg Ile Glu Ser Asp Cys Thr Ile Glu Asp Thr
            340                 345                 350 ttg gtg atg ggc aat gat ttc tac gaa tct tca tca gaa cga gac acc        1104
Leu Val Met Gly Asn Asp Phe Tyr Glu Ser Ser Ser Glu Arg Asp Thr
        355                 360                 365 ctc aaa gcc cgg ggg gaa att gcc gct ggc ata ggt tcc ggc acc act        1152
Leu Lys Ala Arg Gly Glu Ile Ala Ala Gly Ile Gly Ser Gly Thr Thr
    370                 375                 380 atc cgc cga gcc atc atc gac aaa aat gcc cgc atc ggc aaa aac gtc        1200
Ile Arg Arg Ala Ile Ile Asp Lys Asn Ala Arg Ile Gly Lys Asn Val
385                 390                 395                 400 atg att gtc aac aag gaa aat gtc cag gag gct aac cgg gaa gag tta        1248
Met Ile Val Asn Lys Glu Asn Val Gln Glu Ala Asn Arg Glu Glu Leu
                405                 410                 415 ggt ttt tac atc cgc aat ggc atc gta gta gtg att aaa aat gtc acg        1296
Gly Phe Tyr Ile Arg Asn Gly Ile Val Val Val Ile Lys Asn Val Thr
            420                 425                 430 atc gcc gac ggc acg gta atc tag                                         1320
Ile Ala Asp Gly Thr Val Ile
        435

<210> SEQ ID NO 2
<211> LENGTH: 439
<212> TYPE: PRT
<213> ORGANISM: Synechocystis sp. PCC 6803

<400> SEQUENCE: 2

Val Cys Cys Trp Gln Ser Arg Gly Leu Leu Val Lys Arg Val Leu Ala
1               5                   10                  15

Ile Ile Leu Gly Gly Ala Gly Thr Arg Leu Tyr Pro Leu Thr Lys
            20                  25                  30

Leu Arg Ala Lys Pro Ala Val Pro Leu Ala Gly Lys Tyr Arg Leu Ile
        35                  40                  45

Asp Ile Pro Val Ser Asn Cys Ile Asn Ser Glu Ile Val Lys Ile Tyr
    50                  55                  60

Val Leu Thr Gln Phe Asn Ser Ala Ser Leu Asn Arg His Ile Ser Arg
65                  70                  75                  80

Ala Tyr Asn Phe Ser Gly Phe Gln Glu Gly Phe Val Glu Val Leu Ala
                85                  90                  95

Ala Gln Gln Thr Lys Asp Asn Pro Asp Trp Phe Gln Gly Thr Ala Asp
            100                 105                 110

Ala Val Arg Gln Tyr Leu Trp Leu Phe Arg Glu Trp Asp Val Asp Glu
        115                 120                 125

Tyr Leu Ile Leu Ser Gly Asp His Leu Tyr Arg Met Asp Tyr Ala Gln
    130                 135                 140

Phe Val Lys Arg His Arg Glu Thr Asn Ala Asp Ile Thr Leu Ser Val
145                 150                 155                 160

Val Pro Val Asp Asp Arg Lys Ala Pro Glu Leu Gly Leu Met Lys Ile
                165                 170                 175
```

```
Asp Ala Gln Gly Arg Ile Thr Asp Phe Ser Glu Lys Pro Gln Gly Glu
            180                 185                 190

Ala Leu Arg Ala Met Gln Val Asp Thr Ser Val Leu Gly Leu Ser Ala
        195                 200                 205

Glu Lys Ala Lys Leu Asn Pro Tyr Ile Ala Ser Met Gly Ile Tyr Val
    210                 215                 220

Phe Lys Lys Glu Val Leu His Asn Leu Leu Glu Lys Tyr Glu Gly Ala
225                 230                 235                 240

Thr Asp Phe Gly Lys Glu Ile Ile Pro Asp Ser Ala Ser Asp His Asn
                245                 250                 255

Leu Gln Ala Tyr Leu Phe Asp Asp Tyr Trp Glu Asp Ile Gly Thr Ile
            260                 265                 270

Glu Ala Phe Tyr Glu Ala Asn Leu Ala Leu Thr Lys Gln Pro Ser Pro
        275                 280                 285

Asp Phe Ser Phe Tyr Asn Glu Lys Ala Pro Ile Tyr Thr Arg Gly Arg
    290                 295                 300

Tyr Leu Pro Pro Thr Lys Met Leu Asn Ser Thr Val Thr Glu Ser Met
305                 310                 315                 320

Ile Gly Glu Gly Cys Met Ile Lys Gln Cys Arg Ile His His Ser Val
                325                 330                 335

Leu Gly Ile Arg Ser Arg Ile Glu Ser Asp Cys Thr Ile Glu Asp Thr
            340                 345                 350

Leu Val Met Gly Asn Asp Phe Tyr Glu Ser Ser Glu Arg Asp Thr
        355                 360                 365

Leu Lys Ala Arg Gly Glu Ile Ala Ala Gly Ile Gly Ser Gly Thr Thr
    370                 375                 380

Ile Arg Arg Ala Ile Ile Asp Lys Asn Ala Arg Ile Gly Lys Asn Val
385                 390                 395                 400

Met Ile Val Asn Lys Glu Asn Val Gln Glu Ala Asn Arg Glu Glu Leu
                405                 410                 415

Gly Phe Tyr Ile Arg Asn Gly Ile Val Val Ile Lys Asn Val Thr
            420                 425                 430

Ile Ala Asp Gly Thr Val Ile
            435
```

<210> SEQ ID NO 3
<211> LENGTH: 1050
<212> TYPE: DNA
<213> ORGANISM: Pseudomonas syringae
<220> FEATURE:
<221> NAME/KEY: CDS
<222> LOCATION: (1)..(1050)

<400> SEQUENCE: 3

```
atg acc aat ttg caa act ttt gaa tta ccc acc gaa gtg act ggc tgt      48
Met Thr Asn Leu Gln Thr Phe Glu Leu Pro Thr Glu Val Thr Gly Cys
1               5                   10                  15 gcc gct gat att tcc tta ggt cgc gcc ctg att caa gcc tgg cag aaa      96
Ala Ala Asp Ile Ser Leu Gly Arg Ala Leu Ile Gln Ala Trp Gln Lys
                20                  25                  30 gac ggc att ttt caa att aaa acc gat agt gaa caa gac cgt aaa act     144
Asp Gly Ile Phe Gln Ile Lys Thr Asp Ser Glu Gln Asp Arg Lys Thr
            35                  40                  45 caa gaa gct atg gcc gct agc aaa cag ttt tgt aaa gaa ccc ttg acc     192
Gln Glu Ala Met Ala Ala Ser Lys Gln Phe Cys Lys Glu Pro Leu Thr
        50                  55                  60
```

```
ttt aaa tcc agt tgc gtg agc gat tta act tat tct ggc tac gtg gcc      240
Phe Lys Ser Ser Cys Val Ser Asp Leu Thr Tyr Ser Gly Tyr Val Ala
 65                  70                  75                  80 tcc ggt gaa gaa gtt acc gct ggg aaa ccc gac ttt ccc gaa att ttt      288
Ser Gly Glu Glu Val Thr Ala Gly Lys Pro Asp Phe Pro Glu Ile Phe
                 85                  90                  95 acc gtg tgt aaa gat tta tcc gtg ggc gac caa cgg gtt aaa gct gga      336
Thr Val Cys Lys Asp Leu Ser Val Gly Asp Gln Arg Val Lys Ala Gly
            100                 105                 110 tgg ccc tgt cat ggc ccc gtt ccc tgg ccc aac aac acc tac cag aaa      384
Trp Pro Cys His Gly Pro Val Pro Trp Pro Asn Asn Thr Tyr Gln Lys
        115                 120                 125 agt atg aaa act ttt atg gaa gaa ttg ggg tta gcc gga gaa cgc ttg      432
Ser Met Lys Thr Phe Met Glu Glu Leu Gly Leu Ala Gly Glu Arg Leu
130                 135                 140 tta aaa ctg acc gct ttg ggg ttt gaa ctg ccc att aat acc ttt act      480
Leu Lys Leu Thr Ala Leu Gly Phe Glu Leu Pro Ile Asn Thr Phe Thr
145                 150                 155                 160 gat ttg acc cgt gac gga tgg cat cac atg cgc gtg tta cgt ttt ccc      528
Asp Leu Thr Arg Asp Gly Trp His His Met Arg Val Leu Arg Phe Pro
                165                 170                 175 ccc caa acc tcc act ctg agt cgg ggc att ggt gcc cat acc gat tat      576
Pro Gln Thr Ser Thr Leu Ser Arg Gly Ile Gly Ala His Thr Asp Tyr
            180                 185                 190 ggt ctg ttg gtg att gcc gct cag gat gac gtt ggc ggt ctg tac att      624
Gly Leu Leu Val Ile Ala Ala Gln Asp Asp Val Gly Gly Leu Tyr Ile
        195                 200                 205 cgt ccc ccc gtg gaa ggg gaa aaa cgg aat cgc aac tgg ttg ccc ggc      672
Arg Pro Pro Val Glu Gly Glu Lys Arg Asn Arg Asn Trp Leu Pro Gly
210                 215                 220 gaa agc tct gcc ggc atg ttt gaa cat gac gaa ccc tgg acc ttt gtt      720
Glu Ser Ser Ala Gly Met Phe Glu His Asp Glu Pro Trp Thr Phe Val
225                 230                 235                 240 acc ccc act ccc ggg gtg tgg acc gtt ttt ccc gga gat att ctg caa      768
Thr Pro Thr Pro Gly Val Trp Thr Val Phe Pro Gly Asp Ile Leu Gln
                245                 250                 255 ttt atg acc ggg gga cag tta ctg tcc act ccc cat aaa gtg aaa ttg      816
Phe Met Thr Gly Gly Gln Leu Leu Ser Thr Pro His Lys Val Lys Leu
            260                 265                 270 aat acc cgt gaa cgg ttt gcc tgt gct tat ttt cac gaa ccc aac ttt      864
Asn Thr Arg Glu Arg Phe Ala Cys Ala Tyr Phe His Glu Pro Asn Phe
        275                 280                 285 gaa gcc tct gct tac ccc ttg ttt gaa ccc tcc gcc aat gaa cgg att      912
Glu Ala Ser Ala Tyr Pro Leu Phe Glu Pro Ser Ala Asn Glu Arg Ile
290                 295                 300 cat tat ggc gaa cac ttt acc aac atg ttt atg cgg tgc tac ccc gat      960
His Tyr Gly Glu His Phe Thr Asn Met Phe Met Arg Cys Tyr Pro Asp
305                 310                 315                 320 cgc att acc act caa cgt att aac aaa gaa aac cgg tta gcc cat ctg     1008
Arg Ile Thr Thr Gln Arg Ile Asn Lys Glu Asn Arg Leu Ala His Leu
                325                 330                 335 gaa gat ttg aaa aaa tac agt gac acc cgc gct act ggt agc             1050
Glu Asp Leu Lys Lys Tyr Ser Asp Thr Arg Ala Thr Gly Ser
            340                 345                 350
```

<210> SEQ ID NO 4
<211> LENGTH: 350
<212> TYPE: PRT
<213> ORGANISM: Pseudomonas syringae

<400> SEQUENCE: 4

```
Met Thr Asn Leu Gln Thr Phe Glu Leu Pro Thr Val Thr Gly Cys
1               5                   10                  15

Ala Ala Asp Ile Ser Leu Gly Arg Ala Leu Ile Gln Ala Trp Gln Lys
            20                  25                  30

Asp Gly Ile Phe Gln Ile Lys Thr Asp Ser Glu Gln Asp Arg Lys Thr
                35                  40                  45

Gln Glu Ala Met Ala Ala Ser Lys Gln Phe Cys Lys Glu Pro Leu Thr
    50                  55                  60

Phe Lys Ser Ser Cys Val Ser Asp Leu Thr Tyr Ser Gly Tyr Val Ala
65                  70                  75                  80

Ser Gly Glu Glu Val Thr Ala Gly Lys Pro Asp Phe Pro Glu Ile Phe
                85                  90                  95

Thr Val Cys Lys Asp Leu Ser Val Gly Asp Gln Arg Val Lys Ala Gly
                100                 105                 110

Trp Pro Cys His Gly Pro Val Pro Trp Pro Asn Asn Thr Tyr Gln Lys
            115                 120                 125

Ser Met Lys Thr Phe Met Glu Leu Gly Leu Ala Gly Glu Arg Leu
                130                 135                 140

Leu Lys Leu Thr Ala Leu Gly Phe Glu Leu Pro Ile Asn Thr Phe Thr
145                 150                 155                 160

Asp Leu Thr Arg Asp Gly Trp His His Met Arg Val Leu Arg Phe Pro
                165                 170                 175

Pro Gln Thr Ser Thr Leu Ser Arg Gly Ile Gly Ala His Thr Asp Tyr
                180                 185                 190

Gly Leu Leu Val Ile Ala Ala Gln Asp Val Gly Leu Tyr Ile
                195                 200                 205

Arg Pro Pro Val Glu Gly Glu Lys Arg Asn Arg Asn Trp Leu Pro Gly
            210                 215                 220

Glu Ser Ser Ala Gly Met Phe Glu His Asp Glu Pro Trp Thr Phe Val
225                 230                 235                 240

Thr Pro Thr Pro Gly Val Trp Thr Val Phe Pro Gly Asp Ile Leu Gln
                245                 250                 255

Phe Met Thr Gly Gly Gln Leu Leu Ser Thr Pro His Lys Val Lys Leu
            260                 265                 270

Asn Thr Arg Glu Arg Phe Ala Cys Ala Tyr Phe His Glu Pro Asn Phe
            275                 280                 285

Glu Ala Ser Ala Tyr Pro Leu Phe Glu Pro Ser Ala Asn Glu Arg Ile
    290                 295                 300

His Tyr Gly Glu His Phe Thr Asn Met Phe Met Arg Cys Tyr Pro Asp
305                 310                 315                 320

Arg Ile Thr Thr Gln Arg Ile Asn Lys Glu Asn Arg Leu Ala His Leu
                325                 330                 335

Glu Asp Leu Lys Lys Tyr Ser Asp Thr Arg Ala Thr Gly Ser
                340                 345                 350

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
gtcatgccaa tgccgttatc                                                      20
```

<210> SEQ ID NO 6
<211> LENGTH: 47
<212> TYPE: DNA
<213> ORGANISM: Artificial Sequence
<220> FEATURE:
<223> OTHER INFORMATION: PCR Primer

<400> SEQUENCE: 6
catcgttgct gctgcgtaac atttcgaagt caagtttaga acagagg        47

<210> SEQ ID NO 7
<211> LENGTH: 47
<212> TYPE: DNA
<213> ORGANISM: Artificial Sequence
<220> FEATURE:
<223> OTHER INFORMATION: PCR Primer

<400> SEQUENCE: 7
cctcggttct aaacttgact tcgaaatgtt acgcagcagc aacgatg        47

<210> SEQ ID NO 8
<211> LENGTH: 43
<212> TYPE: DNA
<213> ORGANISM: Artificial Sequence
<220> FEATURE:
<223> OTHER INFORMATION: PCR Primer

<400> SEQUENCE: 8
gtgcgaggaa agaaactggc ctaaggtggc ggtacttggg tcg            43

<210> SEQ ID NO 9
<211> LENGTH: 43
<212> TYPE: DNA
<213> ORGANISM: Artificial Sequence
<220> FEATURE:
<223> OTHER INFORMATION: PCR Primer

<400> SEQUENCE: 9
cgacccaagt accgccacct aaggccagtt tctttcctcg cac            43

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
ggtgaacgac aaagccagtt a                                    21

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
cagatggccc gctgtttatt                                      20

<210> SEQ ID NO 12
<211> LENGTH: 20
<212> TYPE: DNA
<213> ORGANISM: Artificial Sequence
<220> FEATURE:
<223> OTHER INFORMATION: PCR Primer

```
<400> SEQUENCE: 12
aacaaccaga ggtattgccg                                              20

<210> SEQ ID NO 13
<211> LENGTH: 19
<212> TYPE: DNA
<213> ORGANISM: Artificial Sequence
<220> FEATURE:
<223> OTHER INFORMATION: PCR Primer

<400> SEQUENCE: 13
aagaagcggt tgttggcgc                                               19

<210> SEQ ID NO 14
<211> LENGTH: 21
<212> TYPE: DNA
<213> ORGANISM: Artificial Sequence
<220> FEATURE:
<223> OTHER INFORMATION: PCR Primer

<400> SEQUENCE: 14
cccattgccc caaaatacat c                                            21
```

BIOLOGICAL PRODUCTION OF ORGANIC COMPOUNDS

CROSS-REFERENCE TO RELATED APPLICATIONS

This application is a continuation of U.S. application Ser. No. 13/560,580, filed Jul. 27, 2012, which claims priority to U.S. Provisional Application No. 61/512,075, filed Jul. 27, 2011, the contents of which are incorporated by reference in their entirety.

CONTRACTUAL ORIGIN

The United States Government has rights in this invention under Contract No. DE-AC36-08GO28308 between the United States Department of Energy and the Alliance for Sustainable Energy, LLC, the Manager and Operator of the National Renewable Energy Laboratory.

REFERENCE TO SEQUENCE LISTING

This application contains a Sequence Listing submitted as an electronic text file entitled "11-18_ST25.txt," having a size in bytes of 20 kb and created on Jul. 27, 2012. Pursuant to 37 CFR §1.52(e)(5), the information contained in the above electronic file is hereby incorporated by reference in its entirety.

BACKGROUND

Using algae or cyanobacteria to produce carbon compounds photosynthetically from $CO_2$ and water has theoretical potential but has yet to be realized on an industrial scale. One major limitation is that these cells are naturally high in protein, especially under conditions that lead to maximum growth rates. Thus a large fraction of carbon from photosynthesis is used to produce nitrogen containing amino acids rather than other products containing only carbon, hydrogen, and oxygen. When nitrogen sources are removed from cultures of non-diazotrophic cyanobacteria, cells accumulate high concentrations of glycogen, but large-scale harvesting of microbial oxygenic phototrophs is difficult and expensive with currently available technologies.

Alpha ketoglutarate (AKG) is used as an organic synthesis intermediate, a medicine ingredient, a biochemical reagent, and as a nutritional additive in food and sport drinks Currently AKG is produced by chemical synthesis using triethyl oxalosuccinic ester derived from petroleum and concentrated hydrochloric acid, or by fermentation using sugar as feedstock. Photosynthetic production of AKG could therefore replace petroleum or sugar as the feedstock and eliminate the use of corrosive acid.

Ethylene is used in the synthesis of diverse products from plastics (e.g., polyethylene, polystyrene, and PVC) to textiles such as polyester. Ethylene has been used to produce high-grade ethanol industrially for the past 50 years, by a relatively simple catalytic process involving the hydration of ethylene into ethanol. In addition, the technology to polymerize ethylene to gasoline has been known for nearly a century. Ethylene is the most widely produced organic compound globally, with more than 132.9 million tons produced in 2010 and projected growth of 5% a year through 2015.

The current method of producing ethylene is via steam cracking of long chain hydrocarbons from petroleum, or via dehydrogenation of ethane. Unfortunately, fossil fuel supplies are finite and utilization of these feed stocks produces greenhouse gases such as $CO_2$ (1.5 to 3.0 tons $CO_2$ per ton of ethylene). For these reasons, sustainable, carbon neutral processes that are capable of producing this essential chemical are needed. One such alternative is the use of biological processes to convert $CO_2$ or other waste products into ethylene. Based on the overall equation $2CO_2 + 2H_2O = C_2H_4 + 3O_2$, photosynthetic production of one ton of ethylene could sequester 3.14 tons of $CO_2$.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide methods for producing alpha ketoglutarate (AKG) or pyruvate by culturing a cyanobacterial cell that lacks a functional ADP-glucose pyrophosphorylase (AGP) enzyme under conditions that allow for AKG or pyruvate production and recovering the AKG or pyruvate from the cyanobacterial cell culture.

In some embodiments, the cyanobacterial cell does not express a functional glgC gene and/or is a *Synechocystis* cell such as a *Synechocystis* sp. PCC 6803 cell.

In certain embodiments, the cyanobacterial cell is cultured under nitrogen starvation conditions in media that does not contain nitrogen. In some embodiments, the concentration of nitrogen in the media is less than about 200 µM. The methods may include a step of adding nitrogen to the media at a final concentration of less than about 1 mM. In certain embodiments, the cyanobacterial cell is cultured under a light intensity of at least about 350 or 600 $\mu E\ m^{-2}\ s^{-1}$.

In further embodiments, the AKG concentration in the culture is greater than 100 mg per liter or 1000 mg per liter. In some embodiment, the pyruvate concentration in the culture is greater than 1 g per liter or 100 g per liter. In certain embodiments, the cyanobacterial cell exhibits at least a 10,000-fold increase in AKG and/or pyruvate production when compared to the wild type cell.

Also provided are cyanobacterial cells that lack a functional ADP-glucose pyrophosphorylase (AGP) enzyme and produce 10,000-fold more AKG or pyruvate when compared to a wild type cell. In some embodiments, the cyanobacterial cells do not express a functional glgC gene and/or are *Synechocystis* cells such as a *Synechocystis* sp. PCC 6803 cells.

Further provided are isolated nucleic acid molecules with sequences at least 90% identical to SEQ ID NO:3 that encode polypeptides that function as ethylene-forming enzymes. In some embodiments, the nucleic acid molecule has a sequence at least 95% identical to SEQ ID NO:3 or has or comprises the sequence of SEQ ID NO:3.

In certain embodiments, the nucleic acid molecule further comprises a promoter such as petE or psbA operably linked to the nucleic acid molecule.

Also provided are expression vectors comprising nucleic acid molecules with sequences at least 90% identical to SEQ ID NO:3 that encode polypeptides that function as ethylene-forming enzymes.

Exemplary embodiments also provide host cells comprising expression vectors described herein or expressing recombinant polypeptides encoded by the nucleic acids described herein. In some embodiments, the host cell is a microbial cell, a cyanobacterial cell, a *Synechocystis* cell or a *Synechocystis* sp. PCC6803 cell. In certain embodiments, the cell maintains a functional copy of the ethylene-forming enzyme for at least four generations. In certain embodiments, the host cells comprise at least one, two, three, four, five or more copies of efe.

Additional embodiments provide methods for producing ethylene comprising culturing a host cell that expresses a recombinant ethylene-forming enzyme under conditions that allow for ethylene production and isolating ethylene from the culture.

In some embodiments, the host cell is a *Synechocystis* cell and expresses a nucleic acid molecule with a sequence at least 90% identical to SEQ ID NO:3.

In certain embodiments, the method further comprises a step of replenishing components of the culture medium that are depleted during the culturing step to the cell culture.

In exemplary embodiments, ethylene is produced at a peak production rate of at least 500 nL mL$^{-1}$ hr$^{-1}$, at least 1 µL mL$^{-1}$ hr$^{-1}$, at least 10 µL mL$^{-1}$ hr$^{-1}$, at least 50 µL mL$^{-1}$ hr$^{-1}$, at least 100 µL mL$^{-1}$ hr$^{-1}$, or at least 200 µL mL$^{-1}$ hr$^{-1}$.

In some embodiments, the step of culturing comprises providing the cell carbon dioxide and light. The light may be sunlight and the carbon dioxide may be atmospheric carbon dioxide.

Further provided are methods for producing ethylene comprising culturing host cells as described herein under conditions that allow for the production of ethylene by the cells and isolating the ethylene produced by the cells.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 2 shows growth curves of batch cultures of *Synechocystis* sp. PCC 6803 cultured in full BG11 media (A) and after suspension in BG11-N media (B). Cultures were under 24 hour light at ~50 µEm$^{-2}$ s$^{-1}$ light flux. Panel (C) shows growth curves for wild type and mutant strains under nitrogen deprivation conditions.

FIG. 5 shows whole-chain net oxygen evolution of cells cultured in BG11-N media normalized to the volume of culture measured (mL) with respect to days nitrogen-starved. Oxygen evolution rates are shown as a percentage of non-nitrogen starved cells. Non-nitrogen starved WT and mutant (AGP–) cultures were within statistical error of each other (~150 µmol O$_2$*(mg Chla)$^{-1}$*hr$^{-1}$). Error bars represent standard deviation of biological replicates (n=3).

FIG. 6 shows relative intracellular concentrations of select metabolites with and without nitrogen starvation (+N or –N) as determined by GC/MS. Y-axis is in units of "normalized ion count," which accounts for the signal response of a 0.1 mg/mL derivatized standard and the dry weight of the sample. Error bars represent standard deviation of biological replicates (n=3).

FIG. 7 shows AKG production (A) over 11 days of culturing in BG11-N media at a cell density of about 0.5 g/L cell dry weight and light flux of about 50 µEm$^{-2}$ s$^{-1}$, and pyruvate production (B) over 5 days under the same conditions. Error bars represent standard deviation of biological replicates (n=3).

FIG. 11 shows the nucleic acid sequence for the glgC gene (A; SEQ ID NO:1) and the amino acid sequence for the AGP protein (B; SEQ ID NO:2).

FIG. 12 illustrates the overall scheme for glgC gene replacement (A) and the assembly of the glgC (shown here as agp) replacement construct using fusion PCR.

FIG. 17 illustrates growth conditions affecting ethylene production. A) Restoration of ethylene production by various additions to a stationary culture that has ceased high-level ethylene production. B) The effect of various medium concentrations on the total ethylene production. C) Refreshing the medium provides a higher rate of ethylene production while allowing the peak production rates to be sustained. Arrows indicate times at which the culture was resuspended in fresh medium. Free squares represent the ethylene production rates of the same culture before resuspension in fresh medium.

FIG. 18 shows a comparison of ethylene production as a function of time (A) or peak production rates (B) from strains harboring one, two, three, or four copies of efe in their genomes. In (A), closed circles represent one copy of efe, closed triangles represent two copies of efe, and the wild type strain is represented by the open circles.

FIG. 19 shows ethylene total productivity (A), specific productivity (B) and growth (C) after resuspension of cultures in fresh 5× BG11 media over multiple weeks. One copy of efe is represented by solid symbols, two copies of efe by open symbols. Panel (D) shows resuspension of a strain harboring two copies of efe in fresh 5× BG11 daily to an $OD_{730}$ of 15.0.

FIG. 20 shows ethylene production under various light conditions. A) Total ethylene productivity from cultures at various light intensities. B) Specific ethylene productivity from cultures at various light intensities.

FIG. 21 shows ethylene total productivity (A), specific productivity (B) and growth (C) under high and low light intensities. A strain with two copies of efe grown at 600 µE $m^{-2}$ $s^{-1}$ is represented by the closed circles, a strain with one copy of efe grown at 600 µE $m^{-2}$ $s^{-1}$ by the open circles, a strain with two copies of efe grown at 50 µE $m^{-2}$ $s^{-1}$ by the open triangles, and a strain with one copy of efe grown at 50 µE $m^{-2}$ $s^{-1}$ by the closed triangles.

FIG. 22 shows the DNA sequence of the efe gene modified for expression in *Synechocystis* 6803 (SEQ ID NO:3). The ATG start codon is illustrated in bold.

FIG. 23 shows the amino acid sequence encoded by the *P. syringae* efe gene (SEQ ID NO:4).

DETAILED DESCRIPTION

Figure 1:
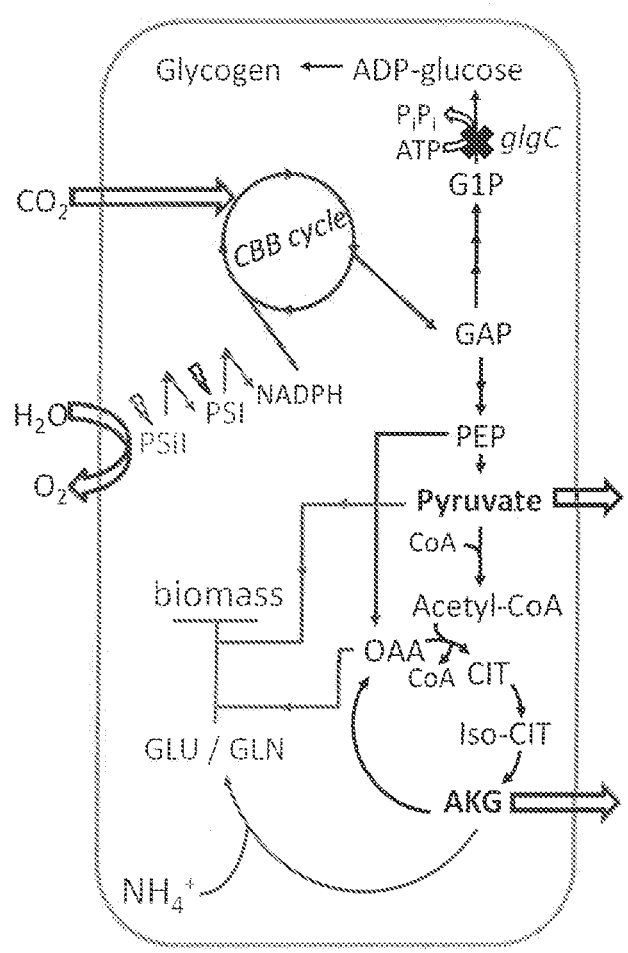
FIG. 1 illustrates the major carbon biosynthetic pathways in cyanobacteria such as *Synechocystis* 6803 under nitrogen-deprived conditions.

Disclosed herein are strains of cyanobacteria that produce high levels of alpha ketoglutarate (AKG) and pyruvate. One example is a mutant strain of *Synechocystis* lacking the glgC gene (FIG. 12A), which does not produce a functional AGP protein (FIG. 12B) or glycogen in detectable levels but overproduces AKG and pyruvate. Methods of culturing these cyanobacteria to produce AKG and pyruvate are also described herein.

*Synechocystis*, a non-diazotrophic *cyanobacterium*, accumulates large amounts of glycogen when starved of nitrogen. While not wishing to be bound to any particular theory, it is believed that carbon flux from photosynthesis can be rerouted away from a storage product (e.g., glycogen) and toward an excreted product (e.g., AKG or pyruvate) by creating stable mutational strains of cyanobacterial cells that are incapable of synthesizing storage products such as glycogen or glucosylglycerol. Such strains include those with disruptions or deletions in the gene that encodes an ADP-glucose pyrophosphorylase (AGP), which catalyzes the conversion of alpha-d-glucose-1-phosphate to adenosine diphosphoglucose (ADP-glucose), the immediate precursor to glycogen. Such AGP-deficient (AGP−) strains may not make detectable amounts of glycogen under nitrogen starvation, but continue to fix carbon photosynthetically at a rate similar to wild-type cells. Yields of AKG and pyruvate in such mutant strains may exceed 100% of the initial cell dry weight of cultures incubated under continuous light in a nitrogen-free growth medium. In *Synechocystis* sp. PCC 6803, a glgC gene (slr1176) encodes an AGP enzyme.

Suitable AGP− strains include those with a genetic mutation to interrupt expression of glgC yet maintain the ability to grow and produce metabolites such as AKG or pyruvate under nitrogen starvation conditions. Additional mutations or deletions in genes in the glycogen synthesis pathway (e.g., glycogen synthase) may also result in the increased production of AKG or pyruvate. Under nitrogen depletion conditions, the mutant strains may produce high levels of AKG, up to or greater than 30% of the cell dry weight, which is on the order of a 10,000-fold increase over the wild type. In certain embodiments, the mutant strains may exhibit at least a 100, 200, 300, 400, 500, 1000, 2500, 5000, 7500, or 10,000-fold increase in AKG production when compared to the wild type strain. In some embodiments, the mutant strains may exhibit at least a 100, 200, 300, 400, 500, 1000, 2500, 5000, 7500, or 10,000-fold increase in pyruvate production when compared to the wild type strain.

The photosynthetic AKG production rate may reach at least 150 grams per day per 1000 liter reactor at a cell density of 1 gram dry weight per liter. Pyruvate can be produced at a rate of at least 275 grams per day per 1000 liter reactor at a cell density of 1 gram dry weight per liter. In some embodiments, AKG or pyruvate production rates may reach at least about 10, 25, 50, 75, 100, 125, 150, 175, 200, 225, 250, 275 or 300 grams per day per 1000 liter reactor at a cell density of 1 gram dry weight per liter. AKG or pyruvate may be harvested from the growth medium without the need to harvest and break cells, thus allowing a continuous "milking" (verses batch culture) process.

AGP− strains may be used for photosynthetic AKG or pyruvate production from only net substrates of $CO_2$, water, and sunlight. A continuous AKG or pyruvate production system in which the culture serves as solar-driven catalyst to convert $CO_2$ to AKG or pyruvate is also contemplated. As there would be no need to harvest cells in such a system, AKG or pyruvate can be harvested continuously or in intervals from the medium. The removal of AKG or pyruvate from the medium may help keep intracellular AKG or pyruvate concentration lower, to prevent possible feedback inhibition, and enhance the rate of production.

The nucleic acid sequence of the glgC gene (SEQ ID NO:1) and the amino acid sequence of the glgC gene product (SEQ ID NO:2) are shown in FIGS. 11A and B, respectively. Exemplary methods for disrupting the glgC gene by fusion PCR are provided in the Examples and figures, but any method suitable for disrupting, ablating or mutating genes in cells may be used. In certain embodiments, all or a portion of the targeted gene is replaced with a selectable marker. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Nucleic acid sequences encoding polypeptides that function as ethylene-forming enzymes and their use in the production of ethylene are also disclosed herein. These nucleic acids may be expressed in hosts such as cyanobacteria, which in turn may be cultured to produce ethylene. For example, methods for using the unicellular cyanobacterium *Synechocystis* sp. PCC 6803 to photosynthetically produce ethylene from atmospheric $CO_2$ are disclosed.

One function of ethylene is as a plant hormone that is involved in regulating numerous processes such as germination, senescence and fruit ripening. In plants, ethylene is synthesized from methionine, which is first converted to S-adenosyl-L-methionine, L-aminocyclopropane-L-carboxylic acid, and finally to ethylene in a three step reaction. Some microbes are also capable of producing ethylene through two pathways not found in plants. Most bacteria generate ethylene from methionine in a two step reaction with a 2-keto-4-methyl-thiobutyric acid intermediate. This reaction, catalyzed by a NADH:Fe(III)EDTA oxidoreductase, is rather inefficient. Many plant pathogens such as *Pseudomonas syringae* synthesize ethylene during infection to weaken their host. In *P. syringae*, ethylene is synthesized from the TCA cycle intermediate, alpha-ketoglutarate, in an efficient single step reaction catalyzed by the ethylene forming enzyme (EFE).

Atmospheric $CO_2$ represents a feedstock that has potential for conversion into other chemicals such as ethanol, biodiesel, or ethylene using photosynthesis. To this end, researchers have attempted to use this process, coupled with EFE, to generate ethylene from atmospheric $CO_2$. Previous attempts have failed due to poor productivity and the inability to stably express EFE (see Fukuda et al., *Biotechnol. Lett.* 16:1-6 (1994); Sakai et al., *J. Ferment. Bioeng.* 84:434-443 (1997); Takahama et al., *J. Biosci. Bioeng.* 95:302-305 (2003)).

Disclosed herein are methods for expressing or overexpressing efe genes (for example, from *P. syringe*) in hosts such as *Synechocystis* to generate strains that are capable of producing ethylene phototrophically. The hosts may express at least one, two, three, four, five or more copies of efe to increase ethylene production rates. These methods overcome two major problems that were previously encountered when using cyanobacteria to produce ethylene: poor stability of efe and poor ethylene productivity. Without wishing to be bound by any particular theory, it has been discovered that removing the mutation hot spots and expressing codon-optimized efe in hosts such as *Synechocystis* alleviates the metabolic burden and stability issues.

The methods disclosed herein allow for the inducible expression of efe, but also allow the utilization of stronger, constitutive promoters like psbA to increase production rates. Other advantages include a decrease in the mutation rate within the coding region of efe and the generation of strains better able to cope with the metabolic drain imposed by ethylene production. The strains generated exhibit little or no inhibition in growth while producing ethylene, nor do they exhibit stress symptoms such as yellowing that had previously been observed in other ethylene-producing strains.

The specific rate of ethylene production typically peaks 24 hours after subculture and then decreases. One or more components of the medium may be a limiting factor in ethylene producing cultures. Ethylene production can be recovered without diluting the culture, by resuspending a stationary phase culture in fresh medium. An increase in ethylene production rate can also be achieved by increasing the concentration of the medium. For example, 10× medium may sustain high level ethylene production longer than 1× medium. Peak rates of about $1500 nL mL^{-1} hr^{-1}$ or greater per genomic copy of efe can be achieved after multiple rounds of resuspension. Total ethylene productivity of a culture may also be increased on a per cell basis by growing the culture in higher light intensities. Light intensities of about 350 µE can be reached in an incubator, but natural sunlight can be many times more intense. Higher ethylene production rates may thus be reached in an outdoor photobioreactor.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

A nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants of SEQ ID NO:3 that encode an ethylene-forming enzyme. For example, a fragment can comprise the minimum nucleotides from SEQ ID NO:3 required to encode a functional ethylene-forming enzyme. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to the sequence represented as SEQ ID NO:3. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:3, or 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:3. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing a query sequences to sequences in publicly available sequence databases (NCBI) using the BLASTN2 algorithm.

Embodiments of the nucleic acids include those that encode a polypeptide that functions as an ethylene-forming enzyme or functional equivalents thereof. For example, the amino acid sequence of the *P. syringae* EFE ethylene-forming enzyme is depicted in FIG. 23 and represented by SEQ ID NO:4. A functional equivalent includes fragments or variants that exhibit the ability to function as an ethylene-forming enzyme. As a result of the degeneracy of the genetic code, many nucleic acid sequences can encode a polypeptide having, for example, the amino acid sequence of SEQ ID NO:4. Such functionally equivalent variants are contemplated herein.

Altered or variant nucleic acids can be produced by one of skill in the art using the sequence data illustrated herein and standard techniques known in the art. Variant nucleic acids may be detected and isolated by hybridization under high stringency conditions or moderate stringency conditions, for example, which are chosen to prevent hybridization of nucleic acids having non-complementary sequences. "Stringency conditions" for hybridizations is a term of art that refers to the conditions of temperature and buffer concentration that permit hybridization of a particular nucleic acid to another nucleic acid in which the first nucleic acid may be perfectly complementary to the second, or the first and second may share some degree of complementarity that is less than perfect.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Oligonucleotides that are fragments of SEQ ID NOS:1 and 3 and antisense nucleic acids that are complementary, in whole or in part, to SEQ ID NOS:1 and 3 are contemplated herein. Oligonucleotides may be used as primers or probes or for any other use known in the art. Antisense nucleic acids may be used, for example, to inhibit gene expression when introduced into a cell or for any other use known in the art. Oligonucleotides and antisense nucleic acids can be produced by standard techniques known in the art.

Also disclosed herein are recombinant vectors, including expression vectors, containing nucleic acids encoding ethylene-forming enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A recombinant vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Recombinant vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule encoding an ethylene-forming enzyme operatively linked to one or more expression control sequences (e.g., transcription control sequences or translation control sequences). In one aspect, an expression vector may comprise a nucleic acid encoding an ethylene-forming enzyme, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. The Examples below illustrate the construction of exemplary expression vectors containing an ethylene-forming enzyme. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the secretion sequences described herein for simple cloning or protein expression.

Certain embodiments may employ cyanobacterial promoters or regulatory operons. For example, a promoter may comprise an rbcLS operon of *Synechococcus*, a cpc operon of *Synechocystis* sp. strain PCC 6714, the tRNApro gene from *Synechococcus*, the nirA promoter from *Synechococcus* sp. strain PCC 7942, which is repressed by ammonium and induced by nitrite. The efficiency of expression may be enhanced by the inclusion of enhancers that are appropriate for the particular cyanobacterial cell system which is used, such as those described in the literature. Suitable promoters also include the petE and psbA promoters.

It will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

The nucleic acids, including parts or all of expression vectors, may be isolated directly from cells, or, alternatively, the polymerase chain reaction (PCR) method can be used to produce the nucleic acids. Primers used for PCR can be synthesized using the sequence information provided herein and can further be designed to introduce appropriate new restriction sites, if desirable, to facilitate incorporation into a given vector for recombinant expression. The nucleic acids can be produced in large quantities by replication in a suitable host cell (e.g., prokaryotic or eukaryotic cells such as bacteria, yeast, insect or mammalian cells). The production and purification of nucleic acids are described, for example, in Sambrook et al., 1989; F. M. Ausubel et al., 1992, Current Protocols in Molecular Biology, J. Wiley and Sons, New York, N.Y.

The nucleic acids described herein may be used in methods for production of AKG, pyruvate or ethylene through incorporation into cells, tissues, or organisms. In some embodiments, a nucleic acid may be incorporated into a vector for expression in suitable host cells. Alternatively, gene-trageting or gene-deletion vectors may also be used to disrupt or ablate a gene. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include photosynthetic bacteria, green algae, and cyanobacteria, including naturally photosynthetic microorganisms or engineered photosynthetic microorganisms. Exemplary microorganisms that are either naturally photosynthetic or can be engineered to be photosynthetic include, but are not limited to, bacteria; fungi; archaea; protists; eukaryotes, such as a green algae; and animals such as plankton, planarian, and amoeba. Examples of naturally occurring photosynthetic microorganisms include *Spirulina maximum*, *Spirulina platensis*, *Dunaliella salina*, *Botrycoccus braunii*, *Chlorella vulgaris*, *Chlorella pyrenoidosa*, *Serenastrum capricomutum*, *Scenedesmus auadricauda*, *Porphyridium cruentum*, *Scenedesmus acutus*, *Dunaliella* sp., *Scenedesmus obliquus*, *Anabaenopsis*, *Aulosira*, *Cylindrospermum*, *Synechoccus* sp., *Synechocystis* sp., and/or *Tolypothrix*.

In exemplary embodiments, the host cell may be a microbial cell, such as a cyanobacterial cell, and may be from any genera or species of cyanobacteria that is genetically manipulable. Examples of suitable cyanobacteria include the genus *Synechocystis* (e.g., strains such as *Synechocystis* sp. PCC 6803), *Synechococcus*, *Thermosynechococcus*, *Nostoc*, *Prochlorococcu*, *Microcystis*, *Anabaena*, *Spirulina*, and *Gloeobacter*.

Further examples of cyanobacteria suitable for use as host cells in the methods described herein include *Chroococcales* cyanobacteria from the genera *Aphanocapsa*, *Aphanothece*, *Chamaesiphon*, *Chroococcus*, *Chroogloeocystis*, *Coelosphaerium*, *Crocosphaera*, *Cyanobacterium*, *Cyanobium*, *Cyanodictyon*, *Cyanosarcina*, *Cyanothece*, *Dactylococcopsis*, *Gloecapsa*, *Gloeothece*, *Merismopedia*, *Microcystis*, *Radiocystis*, *Rhabdoderma*, *Snowella*, *Synychococcus*, *Synechocystis*, *Thermosenechococcus*, and *Woronichinia*; *Nostacales* cyanobacteria from the genera *Anabaena*, *Anabaenopsis*, *Aphanizomenon*, *Aulosira*, *Calothrix*, *Coleodesmium*, *Cyanospira*, *Cylindrospermosis*, *Cylindrospermum*, *Fremyella*, *Gleotrichia*, *Microchaete*, *Nodularia*, *Nostoc*, *Rexia*, *Richelia*, *Scytonema*, *Sprirestis*, and *Toypothrix*; *Oscillatoriales* cyanobacteria from the genera *Arthrospira*, *Geitlerinema*, *Halomicronema*, *Halospirulina*, *Katagnymene*, *Leptolyngbya*, *Limnothrix*, *Lyngbya*,

*Microcoleus, Oscillatoria, Phormidium, Planktothricoides, Planktothrix, Plectonema, Pseudoanabaena/Limnothrix, Schizothrix, Spirulina, Symploca, Trichodesmium,* and *Tychonema; Pleurocapsales* cyanobacteria from the genera *Chroococcidiopsis, Dermocarpa, Dermocarpella, Myxosarcina, Pleurocapsa, Stanieria,* and *Xenococcus; Prochlorophytes* cyanobacteria from the genera *Prochloron, Prochlorococcus,* and *Prochlorothrix;* and *Stigonematales* cyanobacteria from the genera *Capsosira, Chlorogeoepsis, Fischerella, Hapalosiphon, Mastigocladopsis, Nostochopsis, Stigonema, Symphyonema, Symphonemopsis, Umezakia,* and *Westiellopsis*. In certain embodiments, the host cell may be from the genus *Synechococcus*, such as *Synechococcus bigranulatus, Synechococcus elongatus, Synechococcus leopoliensis, Synechococcus lividus, Synechococcus nidulans,* and *Synechococcus rubescens*.

Host cells can be transformed, transfected, or infected as appropriate with gene-disrupting constructs or plasmids (e.g., an expression plasmid) by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing a nucleic acid of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as cyanobacteria by direct transformation, in which DNA is mixed with the cells and taken up without any additional manipulation, by conjugation, electroporation, or other means known in the art. Expression vectors may be expressed by cyanobacteria or other host cells episomally or the gene of interest may be inserted into the chromosome of the host cell to produce cells that stably express the gene with or without the need for selective pressure. For example, expression cassettes may be targeted to neutral cyanobacterial chromosomal sites by double recombination. In certain embodiments, the gene encoding the ethylene-forming enzyme is stable in the host cell for greater than 4, greater than 10, greater than 25, greater than 50 or greater than 100 passages. In some embodiments, the host cell expresses a function copy of the ethylene-forming enzyme for greater than 4, greater than 10, greater than 25, greater than 50 or greater than 100 passages.

Host cells with targeted gene disruptions or carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of producing AKG, pyruvate or ethylene. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors or photobioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing cyanobacteria, for example, are available from ATCC.

Photosynthetic microorganisms may be cultured according to techniques known in the art. For example, cyanobacteria may be cultured or cultivated according to techniques known in the art such as photobioreactor based techniques. One example of typical laboratory culture conditions for cyanobacterium is growth in BG11 medium (ATCC Medium 616) at 30° C., and 5% $CO_2$ under 60 $\mu Em^{-2} s^{-1}$ constant illumination from fluorescent bulbs, with shaking for liquid cultures or without shaking for plates.

Methods for producing AKG, pyruvate or ethylene are also disclosed herein. Cells may be cultured as described above and exposed to a carbon source and light for production of AKG, pyruvate or ethylene. Carbon sources include atmospheric carbon dioxide or carbon dioxide provided from an artificial source such as a compressed storage tank. Cultures may also be provided with additional carbon sources such as sugars (e.g., glucose and other saccharides). For phototrophic AKG, pyruvate or ethylene production, cells may be exposed to either artificial light or natural light such as sunlight. Nitrogen starvation may be achieved by any conventional technique, such as resuspending cells in media containing little or no nitrogenous compounds, or by replenishing depleted media with fresh media containing little or no nitrogenous compounds.

As used herein, "nitrogen starvation conditions" refers to culturing cells in media that is substantially free of nitrogen-containing compounds, for example, culturing cells in nitrogen-depleted media. Nitrogen depleted media or conditions that are substantially nitrogen free refers to media or conditions wherein nitrogen ions are present at levels less than at most 200 $\mu M$. Examples include nitrogen levels of 200, 150, 100, 50, 25 or 10 $\mu M$ or less. In certain embodiments, cells grown in nitrogen-containing media may be subsequently cultured in nitrogen-depleted media (for example, by isolating the cells and resuspending the cells in nitrogen-depleted media, with or without washing the cells in nitrogen-depleted media prior to the resuspension. In some embodiments, cells cultured in nitrogen-containing media may be supplemented with fresh nitrogen-depleted media as the culture progresses.

Nitrogen-containing compounds may be added to cells growing in nitrogen-depleted media to facilitate cell growth. In certain embodiments, nitrogen-containing compounds may be added to cell cultures to a final concentration of less than about 1 mM, or less than about 900, 800, 700, 600, 500, 400, 300, 200, or 100 $\mu M$.

Cell densities, light intensities, medium concentrations, medium compositions and other culture conditions may be varied to achieve peak AKG, pyruvate or ethylene production rates and/or sustain AKG, pyruvate or ethylene production at peak rates. Exemplary light conditions suitable for cell cultures include growth under light (e.g., white light) of at least about 50, 100, 150, 200, 250, 300, 350, 400, 450, 500, 550, 600, 650, or 700 $\mu E\ m^{-2}\ s^{-1}$. Even higher light (e.g., up to about 2000 $\mu E\ m^{-2}\ s^{-1}$) may be suitable for dense cultures, typically with mixing. Examples include 800, 900, 1000, 1100, 1200, 1300, 1400, 1500, 1600, 1700, 1800, 1900, or 2000 $\mu E\ m^{-2}\ s^{-1}$ In certain embodiments, AKG or pyruvate culture concentrations may be at least 100 mg $L^{-1}$. Additional culture concentrations of AKG or pyruvate that may be attained using the methods herein include at least 10, 20, 50, 100, 200, 300, 400, 500, 600, 700, 800, 900, or 1000 mg $L^{-1}$. In some embodiments, AKG concentrations may be greater than 1000 mg $L^{-1}$. For example, AKG concentrations may be at least about 1000, 1500, 2000, 2500, 3000 or 3500 mg $L^{-1}$. Pyruvate concentrations may be at least about 1, 10, 20, 30, 40, 50, 60, 70, 80, 90 or 100 g $L^{-1}$. The peak ethylene production rate is the highest rate of ethylene production attained for a given culture over a given time period. In certain embodiments, ethylene is produced at a peak production rate of at least 500 nL $mL^{-1}$ $hr^{-1}$. Additional peak production rates that may be attained using the methods herein include ethylene is produced at a peak production rate of at least about 1, 5, 10, 25, 50, 75, 100, 150, 200, 250, or 300 μL $mL^{-1}$ $hr^{-1}$. In some embodiments, ethylene may be produced at a peak rate greater than 200 μL $mL^{-1}$ $hr^{-1}$.

Cells may be cultured in batch fermentations and cells that reach stationary phase may be resuspended in fresh medium to continue ethylene production. The medium may be 1× in concentration or may be increased anywhere from 1× to 5× to 10× or greater to support increased production. Alternatively, medium components may be added back to the cultures as they are depleted by the culture and/or waste products may be removed from the cultures as they are produced.

AKG or pyruvate produced by the cell cultures may be released from the cells and collect in the culture media. AKG or pyruvate may be harvested or isolated from the cultures using any means known in the art. For example, the cells may be separated from the culture media and AKG or pyruvate separated from the culture supernatant via conventional separation techniques. Cells may also be lysed and AKG or pyruvate isolated from the cell lysates via conventional separation techniques.

Ethylene produced by the cell cultures is released from the cells and collects in the head space of the culture vessel. Ethylene may be harvested from the cultures using any means known in the art. For example, the culture vessel may contain collection piping to remove ethylene from the head space by active or passive processes. Culture vessel piping may be employed to both provide carbon dioxide to the cells and to remove ethylene produced by the cultures.

EXAMPLES

Example 1

The following materials and methods were used in subsequent Examples detailed below.

Culturing Conditions

*Synechocystis* was cultured at 30° C. in BG11 media (phycology medium, Sigma-Aldrich, USA) supplemented with 20 mM TES buffer and 100 mM $NaHCO_3$ (with or without 3 μM $NiCl_2$) under a constant light flux of approximately 50 to 60 μE $m^{-2}$ $s^{-1}$ supplied by cool white fluorescent lamps. Cultures were shaken (liquid cultures; plates were not shaken) and either bubbled with 2% $CO_2$ in air or under a 5% $CO_2$ headspace in air. When appropriate, plates were supplemented with 50 μg/mL spectinomycin and liquid cultures were supplemented with 25 μg/mL spectinomycin. The antibiotics gentamicin and kanamycin were used at 5 and 50 μg/mL in liquid cultures for inoculation from plates. Thereafter, the antibiotics were removed for growth of cultures in BG11. The same growth conditions were used for nitrogen starved cultures, except that the cells were resuspended in BG11-N media, which is identical to the BG11 medium except that the $NaNO_3$ is replaced with NaCl (mole:mole). Cells were harvested from log-phase cultures in replete medium ($OD_{730}$, 0.6-0.8; DW, 0.3-0.5 g/L) by centrifugation, washed, resuspended in BG11-N and placed under the same light and atmosphere conditions as above.

Optical density was measured at 730 nm with a Biowave II UV/Vis spectrophotometer (Biochrom, Inc., Cambridge, England). Absorbance of whole-cell suspensions of cultures were monitored in a wavelength range of 300-800 nm each day with a spectrophotometer (DU800, Beckman Coulter, USA). Concurrent measurements of dry weight were measured by passing 5 mL culture through 0.45 micron pre-weight filters (Pall Corporation, USA), which were subsequently dried to constant mass at 55° C. for several days and re-weighed.

*E. coli* was grown using standard procedures in LB medium at 37° C., supplemented with 50 μg/mL spectinomycin as appropriate.

Glycogen Content

Glycogen content was measured as described by Ernst et al. (*Archives of Microbiology* 140:120-125 (1984)). Briefly, 1-2 mL of cells were pelleted by centrifugation at 13,000×g for 5 minutes. To each pellet, 200 μL of aqueous KOH (40% by weight) was added. The alkaline suspensions were vortexed and then incubated at 100° C. for 1 hour. Subsequently, 600 μL of cold (0° C.) absolute ethanol was added and this suspension and was centrifuged at 13,000×g. The supernatant was discarded and the pellet was washed with cold ethanol, dried under air at 70° C., and suspended in 1 mL of 200 mM sodium acetate buffer (pH 4.75) containing 10 units amyloglucosidase (Sigma). This solution was incubated at 37° C. for at least 5 hours after which glucose concentrations were determined by a glucose assay kit, which utilizes hexose kinase and NADH (Sigma). Glycogen recovery by this method with known quantities of bovine glycogen (Sigma) was greater than 95%.

Dry Weight Determination

Clear glass bottles (Wheaton, USA) with an approximate capacity of 25 mL were cleaned, acid/base washed, and placed at 55° C. for drying for several weeks. Exactly 50 mL of cells were harvested each day, transferred to 50 mL conical tubes, and centrifuged for 10 minutes at 4,000×g in a swinging bucket rotor. Supernatants were carefully decanted, and approximately 5 mL of deionized water was used to resuspend each of the remaining cell pellets and rinse residual material from conical tubes. Cell suspensions and rinses were transferred to a pre-weighed glass bottle, which was returned to a 55° C. oven for several weeks until all moisture had evaporated (indicated by constant cool dry mass). Weights were measured once for each culture per day. Error bars represent 3 separate cultures.

Photosynthetic Fluorescence Parameters and $O_2$ Evolution

Light-adapted variable fluorescence ΔFv/Fm' measures the effective quantum efficiency of cyanobacteria assuming that the phycobilin content of the cells is similar. A Closed Fluorocam FC-800 C (Photon System Instruments, Czech Republic) was used to measure ΔFv/Fm' daily with respect to nitrogen starvation time under approximately 100 μE $m^{-2}$ $s^{-1}$ light for wild-type and AGP– cultures.

Oxygen Evolution

Whole-chain oxygen evolution for wild-type and AGP– cultures were measured electrochemically with an oxygen electrode system (Photon System Instruments) using a custom microelectrode from Microelectrodes, Inc (New Hampshire, USA). Samples were prepared by centrifuging 7 mL cells from culture and resuspending in 3.5 mL photosynthesis buffer immediately before each time point was collected.

Photosynthesis buffer consisted of 20 mM TES, 100 mM sodium bicarbonate, and 1 mM potassium phosphate. Oxygen concentrations were determined every 100 ms, and the slope of the rise in oxygen concentration in the presence of saturating red light was taken as the relative whole-chain oxygen evolution rate, which was normalized by the difference in voltage between air-saturated buffer and dithionite-treated (anaerobic) buffer.

Intracellular Metabolite Concentrations

To determine metabolite concentrations, 2 mL of cells were centrifuged at 13,000×g for 2 minutes. The cell pellet was then placed on dry ice after decanting the supernatant. Pellets were stored at −80° C. until extraction. For extraction, 2 mL of boiling 70% ethanol in water was poured over the frozen pellet. The mixture was then incubated at 100° C. for 4 minutes and subsequently centrifuged at 13,000×g for 4 minutes. The supernatant in 70% ethanol was dried at 37° C. under a steady stream of nitrogen gas, followed by adding 40 µL of 20 mg/mL methoxyamine hydrochloride in pyridine. The resulting suspension was vortexed for 2 minutes and subsequently incubated at 37° C. for 90 minutes, sealed with Teflon-coated rubber screw-caps. Then, 60 µL MSTFA (N-methyl-N-trimethylsilyltrifluoroacetamide)+1% TMCS (Trimethylchlorosilane) was added to the suspension, followed by vortexing, and sealed incubation for 30 minutes at 55° C.

One microliter of the resulting suspension was injected into a GC/MS (gas chromatograph/mass spectrometer) using a splitless injector. The system used a 7890A GC system and a 5975C inert XL MSD (mass selective detector) with a Tripple Axis Detector (Agilent Technologies Inc., USA). Inlet temperature was 225° C. and compounds were separated using a 30 m DB-35MS column (Agilent Technologies Inc.) with Helium carrier gas and a flow rate of 1 mL/min. GC parameters included 50° C. isothermal heating for 2 minutes followed by a 5° C./min increase to 150° C., a hold for 2 minutes at 150° C., and a second temperature ramping phase of 7° C./min to 320° C. and a 2 minute hold at 320° C. The MSD transfer line was maintained at 280° C. The MS quadrupole and MS source temperature were maintained at 150° C. and 230° C., respectively. Compounds were detected using the scan mode with a mass detection range of 40-500 atomic mass units (amu).

Chromatograms were analyzed with MSD Enhanced ChemStation data analysis software (Agilent Technologies Inc.). Identities of compounds were based on retention time and MS spectral parameters from pre-run standard compounds. Unique m/z ions (target ions) were selected for each compound for manual quantification based on target ion peak areas. Concentration amounts were estimated based on the target ion peak area of the signal relative to this peak response of the pre-run standard at a concentration of 0.1 mg/mL.

Measuring Extracellular AKG Concentrations

High-performance liquid chromatography (HPLC) was used to measure alpha ketoglutarate (AKG) concentrations. Briefly, 2 mL cell suspensions from cultures were taken and passed through a 0.45 µm filter (Pall Corporation, USA). The resulting cell-free solution was used for injection (100 µL) into an Agilent 1200 HPLC. The HPLC was run at 45° C. with a 4 mM aqueous sulfuric acid mobile phase and a Biorad HPLC Organic Acid Analysis (Aminex HPX-87H Ion exchange) column with a refractive index detector. AKG gave a linear response between a concentration range of 25 µM and 10 mM.

The identity of AKG was also confirmed by GC/MS and proton nuclear magnetic resonance (NMR) spectroscopy. The GC/MS protocol for extracellular media was used as described above, except cell media (2 mL) was dried under nitrogen, rather than a 70% cell extract. Proton NMR was measured by drying 2 mL of cell extract in 70% ethanol followed by addition of 1 mL deutorated water (Sigma). From the resulting solution, 600 µL was added to a pyrex NMR tube (5 mm diameter, 7 inch length). The sample was measured with 512 scans in a 500 MHz Varian Spectrometer.

Carbon-13 Isotope Labeling

Cells cultured in (nutrient replete) BG11 were resuspended in BG11-N medium with some sodium bicarbonate replaced with $^{13}C$ sodium bicarbonate (Sigma-Aldrich, USA) as indicated by percentages (final concentration of $^{12}C+^{13}C$ sodium bicarbonate, 100 mM). Cell-free medium following 1-day of growth in BG11-N was collected, and proton NMR spectra were determined as above. Carbon spectra were collected on a 400-MHz Varian spectrometer at 25° C. (18,000 scans with a relaxation delay of 1 s). All spectra were processed using MestReNova software v 6.0.4 (Mestrelab Research S.L., Santiago de Compostela, Spain).

Ethylene Production Assay

Stationary phase cultures were diluted to a starting $OD_{730}$ of approximately 0.2. Each day for the duration of the experiment 2 mL of culture was transferred into a 13 mL Hungate tube and incubated for 4 hours while shaking in 60 $\mu Em^{-2} s^{-1}$ light. The ethylene produced was then quantified using gas chromatography.

Example 2

Mutagenesis and Creation of Mutant Strains

As depicted in FIG. 12, fusion PCR was used to create a gene deletion DNA fragment that was composed of approximately 600 by immediately upstream the glgC gene fused to a DNA fragment of the genR coding sequences from the pUC119 DNA followed by approximately 600 by immediately downstream the glgC gene. This construct was transformed into a glucose tolerant strain of *Synechocystis* and selected over time on standard BG11 agar plates containing gentamicin. Transgenic lines were screened by PCR followed by western blot and glycogen assay for a complete depletion of the glgC gene, AGP protein and glycogen, respectively. Herein we refer to the generated mutant strain as the AGP− strain as an indication that this strain lacks an ADP-glucose pyrophosphorylase.

Figure 13:
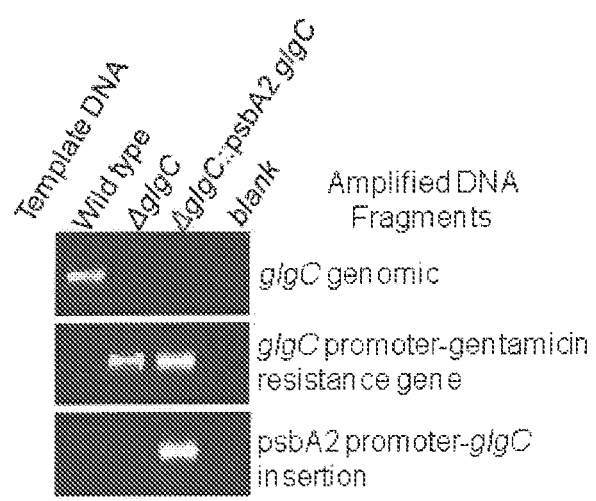
FIG. 13 shows a PCR analysis illustrating that the glgC genomic fragment is only detectable in the wild type genome.
Figure 14:
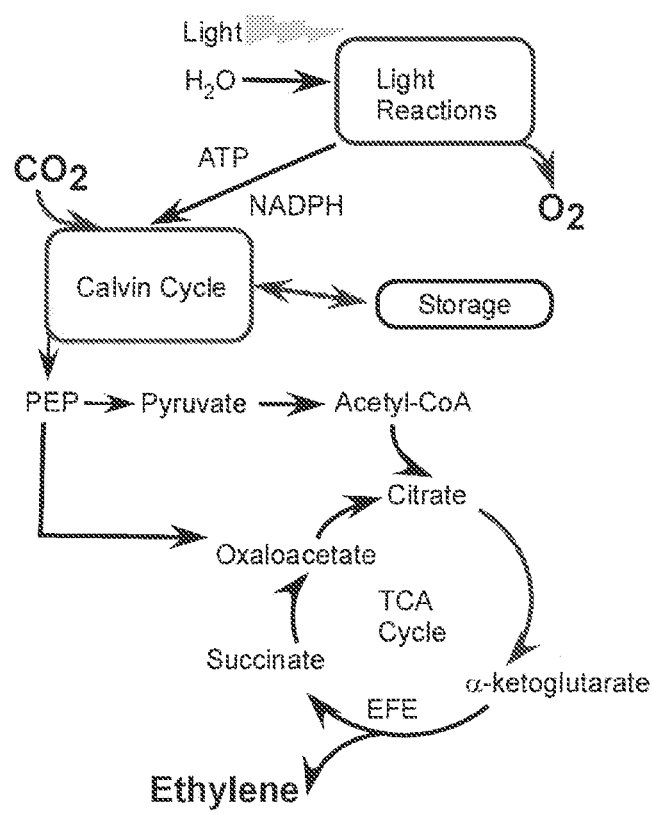
FIG. 14 illustrates a pathway for the synthesis of ethylene via an ethylene forming enzyme (EFE) that converts α-ketoglutarate, a key metabolite in the citric acid cycle, to ethylene.

A specific ORF replacement of the glgC gene (slr1176) with a gentamicin-resistance gene was performed using homologous recombination. A gene deletion construct was created using fusion PCR that contained flanking regions of the glgC gene and the pUC119-gen plasmid (PCR primers described in Table 1), using KOD Hot Start DNA Polymerase (Novogen) under standard conditions. Transformation of wild type was performed using the created gene-deletion construct. Selection was performed on agar plates with BG-11 (10 mM $NaHCO_3$, gentamicin between 20 and 50 µg/mL). Segregation of the mutation was verified by PCR product analysis (FIG. 13) using primers listed in Table 1. Glycogen determination, glucosylglycerol determination by HPLC, and western blot protein analysis demonstrated that the glgC mutant is a fully segregated mutant. For western blotting, protein was isolated from logarithmically growing cultures, extracted, and quantified. Proteins were separated using Mini Protean TGX Gels (Biorad), and blotted using Fast Semi Dry Blotter (Pierce) onto PVDF (Biorad) membranes. A custom peptide primary antibody for GlgC (Yen-Zym Antibodies, LLC) was used in conjunction with Goat Anti-Rabbit secondary antibody (Pierce) and a CN/DAB Substrate Kit (Thermo Scientific).

*Synechocystis* sp. PCC 6803 strain ΔglgC psbA2::glgC was constructed from the ΔglgC line above with the pPSBA2KS vector altered by removal of the SalI site via partial digest and blunting to allow for retention of the kanamycin resistance gene. The glgC gene was amplified from genomic DNA isolated from WT by PCR and inserted into the vector between the NdeI and SalI restriction sites. Transformation was conducted by incubation of approximately 1 μg of the integration vector for 6 hours with 200 μL cells (adjusted to optical density of 2.5 from logarithmic-phase cultures), followed by addition of 2 mL BG11, 24 hours outgrowth in culture tubes under standard growth conditions, and plating of 200 μL on BG11 plates with 200 μg/mL kanamycin. The mutation was verified by PCR product analysis using primers listed in Table 1.

TABLE 1

| | | SEQ ID NOs |
|---|---|---|
| Fusion PCR Primers | | |
| 5'agpF | GTCATGCCAATGCCGTTATC | SEQ ID NO: 5 |
| agp/gn atgR | CATCGTTGCTGCTGCGTAACATTTCGAAGTCAAGTTTAGAACAGAGG | SEQ ID NO: 6 |
| agp/gn atgF | CCTCGGTTCTAAACTTGACTTCGAAATGTTACGCAGCAGCAACGATG | SEQ ID NO: 7 |
| agp/gn taaR | GTGCGAGGAAAGAAACTGGCCTAAGGTGGCGGTACTTGGGTCG | SEQ ID NO: 8 |
| agp/gn taaF | CGACCCAAGTACCGCCACCTAAGGCCAGTTTCTTTCCTCGCAC | SEQ ID NO: 9 |
| 3'agpR | GGTGAACGACAAAGCCAGTTA | SEQ ID NO: 10 |
| Genomic Segregation Screening | | |
| 5'outagpF | CAGATGGCCCGCTGTTTATT | SEQ ID NO: 11 |
| agpR | AACAACCAGAGGTATTGCCG | SEQ ID NO: 12 |
| GentintR | AAGAAGCGGTTGTTGGCGC | SEQ ID NO: 13 |
| PsbA2outF | CCCATTGCCCCAAAATACATC | SEQ ID NO: 14 |

Example 3

Growth Properties of Cyanobacterial Strains

Figure 9:
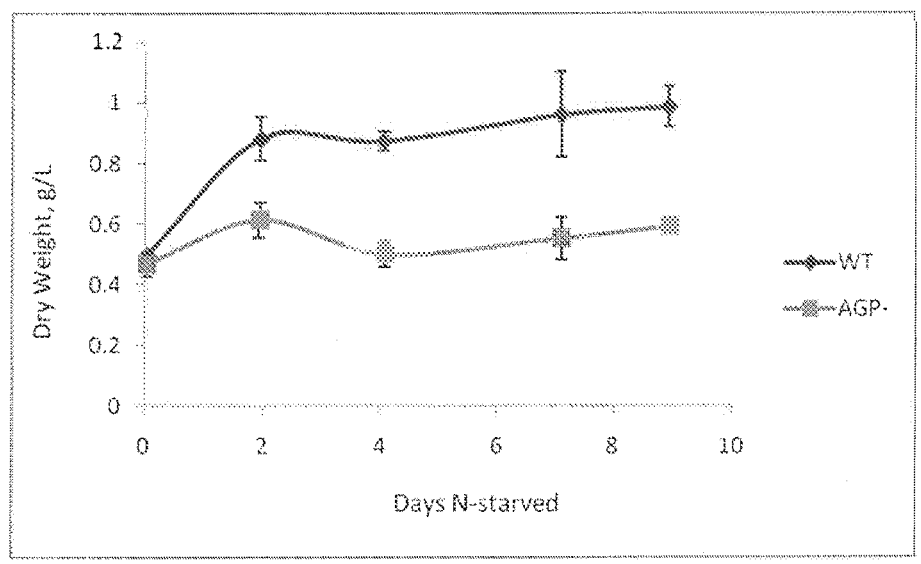
FIG. 9 shows dry weights of WT and AGP– cultures incubated for up to 9 days in BG11-N.

As shown in FIG. 2A, the growth rates of wild-type and AGP− cultures in full-nitrate medium are nearly identical. However, these strains behave differently under nitrogen starvation (FIGS. 2B and C). Wild-type cultures of *Synechocystis* 6803 nearly double in optical density (FIG. 2B) before reaching a steady state over 5 days of incubation in BG11-N. This behavior mimics the trends seen for dry weight measurements taken over a period of nitrogen arrest (FIG. 9). The AGP− strain remains blue-green over this period of time, and does not increase in optical density or cell dry weight. Nitrogen starvation of *Synechocystis* sp. PCC 6803 and other non-diazotrophic cyanobacteria typically leads to a reduction in phycobilin proteins, resulting in a culture color change from blue-green to yellow-green, a process sometimes referred to as "bleaching".

Example 4

Cyanobacterial Strain Characteristics

Figure 3:
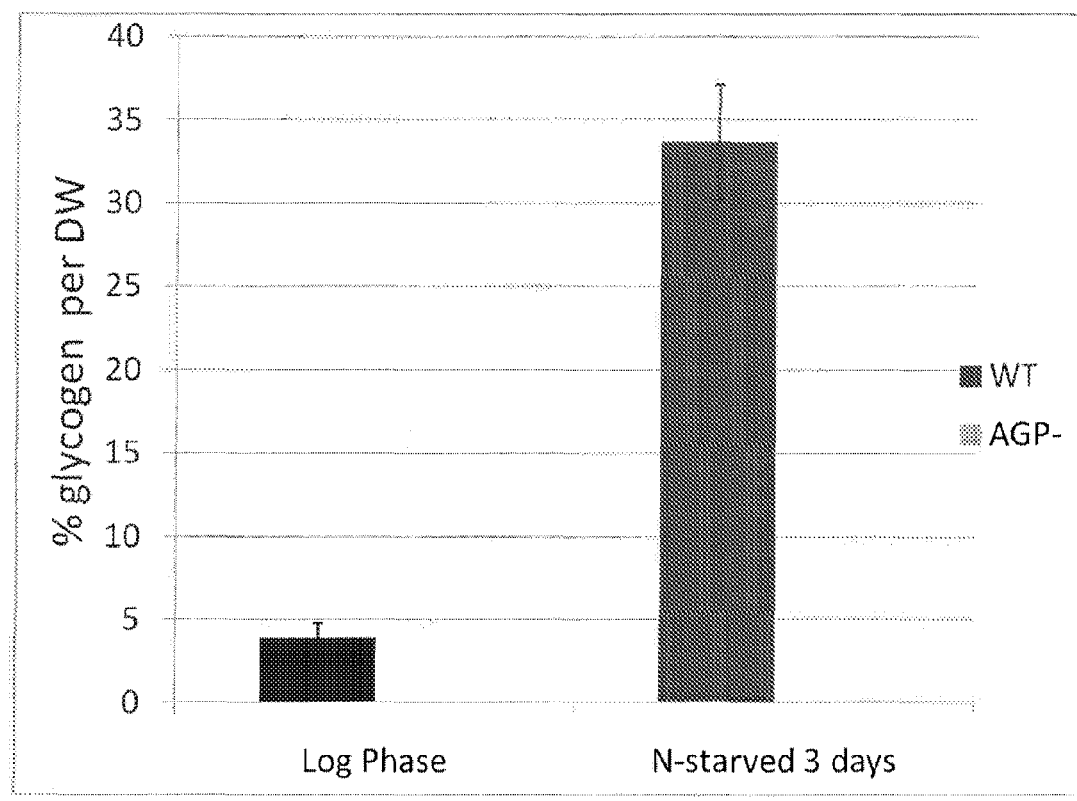
FIG. 3 shows glycogen content of cultures from log phase (growing in BG11) and after incubation in BG11-N for 3 days. No glycogen was detected for the AGP– strain in either condition. Error bars represent standard deviation of biological replicates (n=3).

FIG. 3 displays glycogen content as a percentage of cell dry weight in both wild-type (WT) and AGP− strains under growth in BG11 or incubation in BG11-N. No detectable amounts of glycogen were observed in the AGP− strain under either condition (detection limit 0.2% of dry weight), but the glycogen content of wild-type cells nearly tripled after 3 days of incubation in BG11-N. That the optical densities and dry weights (FIGS. 8 and 9) of AGP− cultures do not substantially change over the course of nitrogen starvation suggests two possibilities: (1) photosynthesis of the AGP− strain fixes no (or very little) net carbon, or (2) the AGP− strain is producing another product from its fixed carbon that does not contribute to cell dry weight (e.g. is excreted into the medium).

Figure 4:
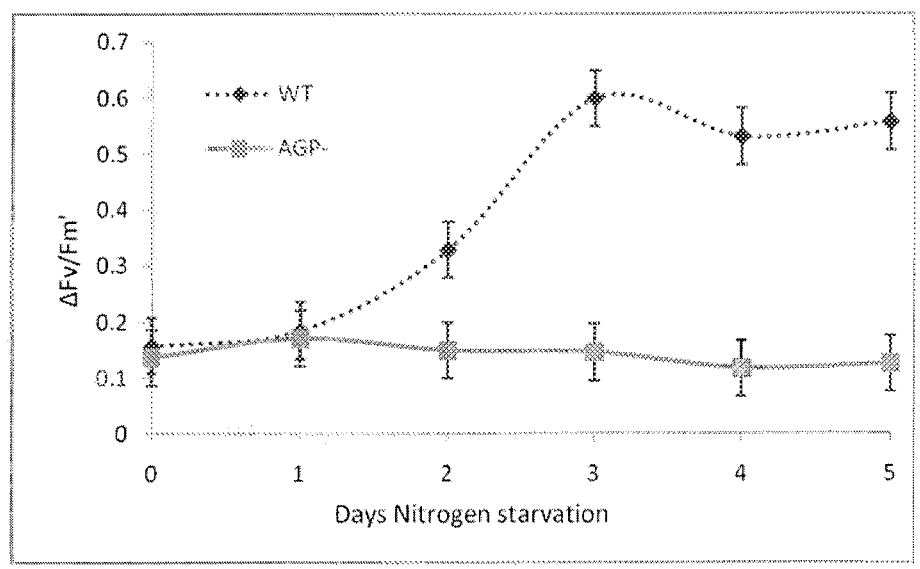
FIG. 4 illustrates light-adapted quantum efficiency (Fv'/Fm') of cells cultured in BG11-N media for up to 5 days. Wild type (WT) is shown as dashed line because of phycobilin changes that artificially increase the measured value. Error bars represent standard deviation of biological replicates (n=3).
Figure 10:
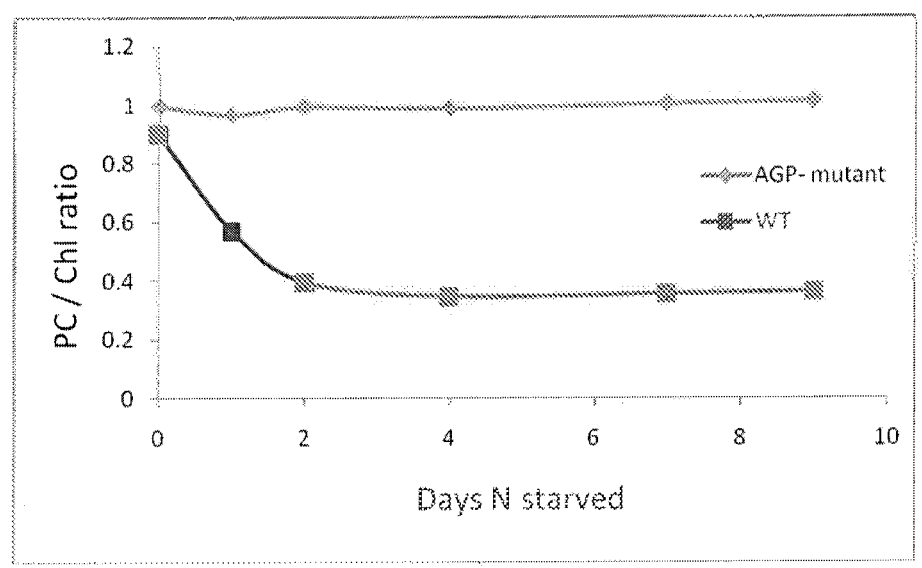
FIG. 10 illustrates absorbance of whole cell suspensions at 630 nm divided by absorbance at 680 nm, used to estimate phycobilin (PC)/Chlorophyll ratio in cells with respect to days of incubation in BG11-N.

To investigate these two possibilities, the effective quantum efficiency of light-adapted cells (a relative indicator of photochemical reactions) was examined under a constant light source (FIG. 4). This measurement can be reliably obtained from cyanobacterial cells that do not change phycobilin content, which appeared to be the case for the AGP− strain, as the color of these cultures does not change with respect to time, and the absorbencies of whole-cell suspensions at 630 nm (phycobilins) and 680 nm (chlorophyll) do not change substantially in the AGP− strain (FIG. 10). The light-adapted quantum efficiency (ΔF/Fm') for AGP− cells remains relatively constant for up to 5 days incubation in BG11-N(FIG. 4). This may indicate that photosynthesis under non-saturating light (~100 μE m$^{-2}$ s$^{-1}$) leads to continuous fixation of $CO_2$ at the same rate at non-nitrogen starved conditions (time=0 days) as after 5 days of nitrogen starvation (time=5 days).

The relationship between photosynthetic capacity and nitrogen starvation was also examined. Whole-chain oxygen evolution under saturating light conditions was measured for wild-type and AGP− cultures (FIG. 5). Evolution rates are reported as a percentage of non-nitrogen starved cultures (day 0 cultures), but evolution rates normalized to chlorophyll content at this time point were within error (~200 μmol $O_2$ mg chla$^{-1}$ hr$^{-1}$). Normalizing to chlorophyll content was not appropriate for cultures starved of nitrogen for any period of time, as chlorophyll concentrations degrade slightly with nitrogen starvation, which would artificially increase apparent evolution rates. FIG. 5 shows that $O_2$ evolution rates of both wild-type and AGP− cultures decline. However, the AGP− cultures decline at a rate similar to or slower than that of the wild-type. These results indicate that AGP deletion also causes a non-bleaching phenotype under nitrogen starvation, but does not lead to significantly higher decline in photosynthesis capacity relative to the wild-type strain. This in turn suggests that the cells are fixing $CO_2$ and directing the resulting photosynthate into a product that does not contribute to dry weight.

Example 5

AKG Production

Intracellular concentrations of some metabolites in both wild-type and AGP− strains were measured by GC/MS for log-phase (nitrogen replete) and nitrogen starved (2-days) cultures. Previous results suggested that a fraction of photosynthate may have been redirected into sucrose, a known secondary osmolyte, which has been shown to increase in some salt-treated cells of *Synechocystis* 6803. FIG. 6A shows that this is not the case, as the AGP− cultures in both N+ and N− conditions have less sucrose than wild-type strains. Measurements of some citric acid cycle intermediates (citric acid, fumaric acid, and alpha ketoglutarate) indicate that flux has instead been directed (at least in part) to the citric acid cycle in APG− cultures lacking nitrogen (FIGS. 6B-D). In the absence of available nitrogen from growth media (in the form of ammonium, nitrate, or urea) or from phycobilin degradation, AKG, which is produced irreversibly from isocitrate via isocitrate dehydrogenase, is a "dead end" product. In other words, AKG apparently cannot be further metabolized by cells in the absence of $NH_4^+$, and therefore accumulates to high concentrations. In fact, AKG is known to be the signaling molecule for sensing carbon:nitrogen ratio status intracellularly in cyanobacteria.

Examination of extracellular media by HPLC revealed a substantial accumulation of AKG in nitrogen-starved AGP− cultures (FIG. 7). The identity of this extracellular metabolite was confirmed by GC/MS (of derivatized dried cell media). Proton NMR spectra of ethanol extracts of nitrogen-starved AGP− cells also showed a high abundance of AKG. For approximately 4-5 days of incubation in BG11-N, linear amounts of AKG are produced—consistent with the observation that low-light photosynthesis effective quantum yield is constant for this period of time (FIG. 4).

Figure 8:
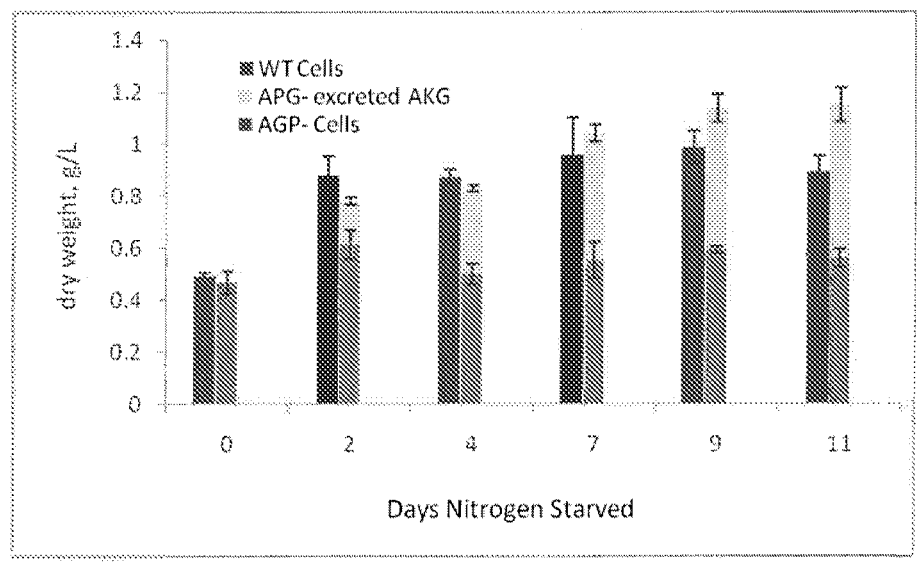
FIG. 8 shows total dry weight of photosynthetically produced material over 11 days of nitrogen starvation. Wild-type (WT) cells produced nearly undetectable levels of excreted AKG, while a significant amount of AKG was produced by the AGP– mutant strain and is stacked over total cell dry weight to show total dry weight material produced.

FIG. 8 illustrates the redistribution of mass from cellular constituents in the wild-type strain, to excreted alpha ketoglutarate in the AGP− strain. While the total amount of material made photosynthetically from the AGP− strain (sum of stacked values) is similar to that of wild-type dry weight, approximately 50% of the total amount of mass is in the form of one excreted product in the AGP− strain: alpha ketoglutarate.

Example 6

Pyruvate Production

Proton NMR studies indicating the presence of AKG also revealed two additional peaks in this material, at ppm shifts of 2.38 and 1.44 relative to the NMR internal standard trimethylsilyl propionate, TSP. We designed a medium that is proton NMR silent. That is, the cells were suspended in a medium that does not have abundant peaks by proton NMR and incubated under standard nitrogen starvation conditions. (Our standard BG-11 medium uses TES buffer, citric acid, and ETDA, all of which have proton NMR signatures; the new buffer is standard BG-11 with $NaNO_3$ replaced with NaCl, mole for mole, and with TES, citric acid, and $Na_2EDTA$ removed with no substitutions). In doing so, additional peaks were observed in this buffer that grew with respect to days of nitrogen starvation.

The predominant peak is at a shift (with respect to TSP) of 2.36 ppm. This peak can be matched to either succinate or pyruvate in proton NMR libraries. However, an additional peak is found at 1.47 ppm that is not present in succinate standards. Samples of NMR-silent buffers in which cells had been nitrogen starved revealed a new peak, previously unidentified because it has the same retention time as TES. A standard of sodium pyruvate was prepared in this buffer and had a matching retention time. Thus, HPLC and proton NMR analyses confirmed that pyruvate is a second metabolite produced by AGP− cells under nitrogen starvation. Pyruvate and AKG account for approximately 85+/−11% of fixed carbon.

Example 7

Construction of Stable, Ethylene Producing Strains of *Synechocystis*

To generate petE:EFE, a modified *P. syringae* efe gene was synthesized in pUC57 vector. The efe coding region was excised from pUC57 with LguI and transferred to pPETE cut with the same enzyme. This placed efe under the control of the plasmid-born petE promoter. This plasmid was named pJU101. pJU101 was then integrated into the chromosome of *Synechocystis* via double recombination into the slr0168 region as previously described (Zang et al., J. Microbiol. 45:241-245 (2007)). To generate psbA:EFE, the 5' end of the modified efe was synthesized, with the first 75 by of the pea plant chloroplast psbA promoter attached in vector pUC57. The psbA promoter and efe coding region were excised from pUC57 with SmaI and BsrGI and transferred to pJU101 cut with the same enzymes. This restored the full coding region of efe while simultaneously replacing the petE promoter with the psbA promoter. This plasmid, named pJU102, was then integrated into the chromosomes of *Synechocystis* via double recombination into the slr0168 region.

To make a second plasmid for integration into an alternate genomic site, efe was cloned from pJU102, cut with EcoRI and XhoI, and placed into the SalI and NcoI sites of pPSBA2KS. This plasmid, named pJU112, was then integrated into the chromosomes of the *Synechocystis* containing the first copy of efe via double recombination into the psbA2 locus to generate the 2× psbA: Sy-efe strain.

Previous attempts to engineer cyanobacteria to produce ethylene were unsuccessful because the efe gene was readily inactivated within three generations of successive culture growth (see Takahama et al., J. Biosci. Bioeng. 95:302-305 (2003)). Inactivation of the efe gene appeared to result from specific duplications at certain mutation hot spots within the gene, leading to truncated peptides. To overcome this stability issue, several silent mutations were made in the *P. syringae* efe sequence that eliminated the potential mutation hotspots while retaining the correct amino acid sequence of EFE. In addition, we codon-optimized the sequence of efe for improved expression in *Synechocystis*.

The nucleic acid sequence of the modified efe gene is shown in FIG. 22 and is represented as SEQ ID NO:3. The amino acid sequence of the product of the modified efe gene is shown in FIG. 23 and is represented as SEQ ID NO:4. The modified efe was placed under the control of either the copper regulated petE promoter or the constitutive pea plant psbA promoter. The efe gene and an accompanying spectinomycin resistance cassette were inserted into the chromosome of *Synechocystis* at a neutral site (slr0168) via double recombination.

Figure 15:
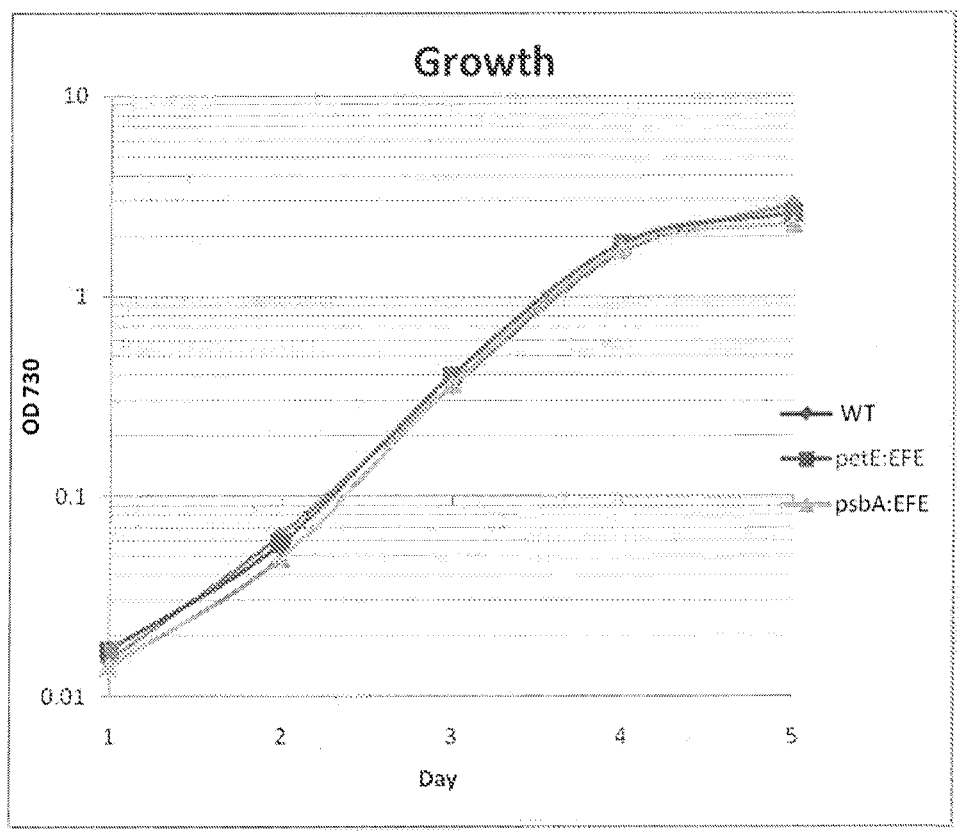
FIG. 15 shows growth rates of threes strains of *Synechocystis* 6803.

A second source of instability of efe in previous studies was the apparent metabolic burden that ethylene production imposed on the organism. Previous work showed that EFE significantly reduced a strain's specific growth rate, thereby applying a strong selection pressure for cells that harbor non-functional copies of efe (see Sakai et al., *J. Ferment. Bioeng.* 84:434-443 (1997) and Takahama et al., *J. Biosci. Bioeng.* 95:302-305 (2003)). Colonies expressing a functional copy of efe also appeared yellow, indicating stress caused be expression of the efe gene. The modified efe gene was expressed in *Synechocystis* and no repression of growth rate was observed (see FIG. 15), suggesting no or less metabolic burden resulting from EFE. This reduced selection against functional copies of efe, resulting in increased stability of efe in the efe-expressing *Synechocystis* strains. Additionally, ethylene-producing colonies of *Synechocystis* appeared indiscernible from wild-type colonies of the same strain, further suggesting decreased metabolic stress from EFE expression.

Example 8

Ethylene Production Driven by the petE and psbA Promoters

The modified efe was initially expressed under the control of the copper-inducible petE promoter to impart stability to the system by not inducing expression of efe until stationary phase. For comparison, modified efe was also expressed from the pea plant chloroplast genome psbA constitutive promoter. Ethylene production rates of the two recombinant strains were compared using gas chromatography and ethylene production was observed to peak early in growth and then fall off as the culture enters stationary phase (see FIG. 16A). Diluting the stationary cultures with fresh medium reinitiated log phase growth and restored peak ethylene production rates (See FIG. 16B). These data suggest that the observed decrease in ethylene production was not due to inactivation of the efe gene.

Higher EFE protein levels were also observed with the expression of efe from the psbA promoter compared to the petE promoter. The increase in expression from the psbA promoter was corroborated by a 10-fold higher ethylene production from this strain (see FIG. 16A). The psbA:EFE lines were then examined to determine if ethylene production could be stably maintained over several generations in this strain. In order to examine stability of this ethylene producing strain, the cultures were serially passed through 4 generations of growth and ethylene production was measured daily for 10 days with each generation. In contrast to previous studies in which the ability of a culture to produce ethylene decreased over successive generations and had completely disappeared after three generations (Takahama et al., *J. Biosci. Bioeng.* 95:302-305 (2003)), consistent rates of ethylene production were maintained through the course of 4 serial passages of the same culture (see FIG. 16B). This suggests that the *Synechocystis* strain was capable of maintaining a functional copy of the modified efe gene over multiple serial passages of the culture.

Example 9

Effect of Medium on Ethylene Production

Figure 16:
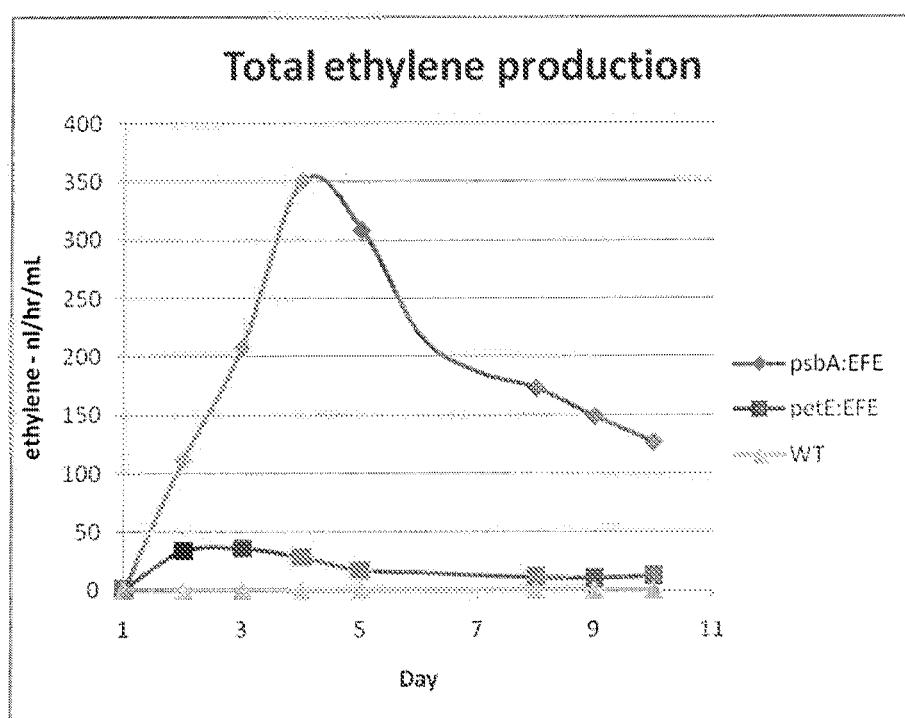
FIG. 16 shows ethylene production from *Synechocystis* 6803 harboring an efe gene. A) Comparison of ethylene production rates when efe is expressed from either the petE or the psbA promoters. B) Ethylene production normalized to density and total ethylene production (C) of *Synechocystis* 6803 expressing efe from the psbA promoter across four consecutive cultures.

Ethylene production peaks early in the culture's growth period and typically falls off as the culture ages (see FIG. 16B). Ethylene production rates were restored each time in successive subculture, indicating that the decrease in ethylene production was not due to inactivation of efe. One possible reason for the apparent decrease in ethylene production is that light, carbon, or another nutrient becomes limiting as the culture reaches stationary phase. In order to elucidate the limiting component(s) for ethylene production, a stationary phase culture in which ethylene production had nearly ceased was divided and transferred to cultures with high light (150 $\mu Em^{-2}\, s^{-1}$) exposure, added additional nitrogen, or fresh growth medium.

The culture that was supplemented with additional ammonium displayed a repressed ethylene production rate compared to the control (see FIG. 17A). The culture that was transferred to high light reached a significantly higher density. However, this culture produced a similar amount of ethylene as the control despite the fact that there were 1.5 times as many cells in the culture. In contrast, the culture that was resuspended in fresh medium reached a similar density as the control yet produced more ethylene. Collectively, these findings suggest that maximum cell density and ethylene production are limited by independent factors, with light limiting the final cell density and component(s) of the medium limiting ethylene production.

To determine whether increasing the medium concentration could further stimulate ethylene production, medium concentrations ranging between 1× and 10× were tested. Increasing the medium concentration as much as 10-fold indeed promoted increasing rates of ethylene production (see FIG. 17B). 10× medium led to a 2-fold increase in total ethylene production relative to 1× medium, producing a peak rate of 700 nL mL$^{-1}$ hr$^{-1}$.

The ability of medium replenishment to restore ethylene production from a culture that had ceased to produce ethylene was also investigated. A stationary phase culture that had lost its ability to produce ethylene was resuspended in fresh 5× medium at the beginning of each week for a month. Ethylene production was measured each day over the course of the experiment. Ethylene production from a small sample of the culture was also measured before it was resuspended to confirm that the culture had ceased to produce high levels of ethylene prior to resuspension. High-level ethylene production was determined to resume immediately after resuspension in fresh medium; reaching a peak three days later and then declining thereafter. Additionally, each time the medium was refreshed, the peak production rate for that culture also increased, eventually reaching a maximum of 1500 nL mL$^{-1}$ hr$^{-1}$ (see FIG. 17C). These findings suggest that a culture will maintain high-level ethylene production provided the problem of medium limitation is alleviated.

Example 10

Expression of Multiple Copies of EFE

Because expression of EFE produced no apparent metabolic burden on *Synechocystis*, ethylene production in strains expressing a second copy of efe was investigated. The second copy of efe was also under control of the pea plant psbA promoter, and was integrated into the *Synechocystis* genome at the psbA2 locus along with a kanamycin resistance cassette. Increased expression of EFE was verified by Western blotting. Comparison of ethylene production between strains with a single or double copy of efe showed that a second copy of efe doubled the ethylene output (FIG. 18). Furthermore, the strain with a second copy of efe exhibited growth characteristics similar to wild type (Table 2), suggesting that increased ethylene production does not pose a severe metabolic burden.

TABLE 2

| Strain | Generation time (h) |
| --- | --- |
| wild type | 10.7 +/– 0.41 |
| psbA: Sy-efe | 11.0 +/– 0.58 |
| 2X psbA: Sy-efe | 10.9 +/– 0.63 |

Example 11

Ethylene Production in Semi-Continuous Culture

Since depletion of medium components limits ethylene productivity, regular medium replenishment should sustain high level production. To test this, ethylene production in semi-continuous culture expressing either one or two copies of efe was examined. A stationary-phase culture was diluted to an $OD_{730}$ of 0.25, allowing it to resume log phase growth. Seven days later, the culture reached stationary phase and ceased producing significant amounts of ethylene. The culture was then spun down and resuspended at the same cell concentration in fresh 5× BG11. The process of resuspending the previous culture (without dilution) in fresh 5× BG11 was repeated weekly for 3 additional weeks. Ethylene production was measured each day over the course of the experiment. High-level ethylene production resumed immediately after resuspension in fresh medium, reaching a peak 24 hours later and declined thereafter (FIG. 19). Each time the medium was refreshed, growth resumed, and the peak production rate for that culture also increased, eventually reaching a maximum of 3100 $\mu L\ L^{-1}\ h^{-1}$ at $OD_{730}$ of approximately 20. Specific activity generally decreased as the culture density increased, but was more than offset by the increase in culture density, resulting in higher total production from high density cultures.

Weekly media replacement was insufficient to sustain ethylene production at the peak level (3100 $\mu L\ L^{-1}\ h^{-1}$) for longer than one day; thus conditions more closely resembling continuous culture were investigated to determine if this would extend ethylene production at the maximum rate. Daily media refreshment was performed to maintain a specific culture density. A culture expressing two copies of efe was concentrated to an initial density of $OD_{730}$ 15.0. Each day for three weeks the culture was spun down and resuspended at this same density; ethylene production was measured after each resuspension. Under these conditions the peak production rate of 3100 $\mu L\ L^{-1}\ h^{-1}$ was maintained continuously (FIG. 19). This finding indicates that the peak rates reported in this study resemble the continuous rate that can be expected using continuous culture.

Example 12

Effect of Light Intensity on Ethylene Production

Increases in total productivity can be achieved by using cultures of increasing density. The potential to obtain a similar increase in production on a per cell basis was also investigated. Growing cells at very high density can result in light limitation due to self shading, so alleviating this limitation could increase the specific productivity. The effect of various light intensities, up to 350 μE, on specific ethylene production was examined. The results presented in FIG. 20B demonstrate that specific productivity increases with increasing light intensity. With high light intensity, a measured total productivity of 2500 $nL\ mL^{-1}\ hr^{-1}$ was achieved (see FIG. 20A). This production rate resulted from a combination of increased specific productivity while maintaining the high culture density that previously yielded a production rate of 1500 $nL\ mL^{-1}\ hr^{-1}$, rather than just using more cells to generate increasing ethylene production rates.

The effect of high light (600 $\mu E\ m^{-2}\ s^{-1}$) on ethylene production rates of high cell density ($OD_{730}$ ~15.0) was also examined. Cultures expressing either one or two copies of efe were resuspended in fresh 5× BG11 to a density of $OD_{730}$ approximately 15 and placed under all white Diamond series LED lights (Advanced LED Lights) with 600 $\mu E\ m^{-2}\ s^{-1}$ reaching the culture. Ethylene production was measured daily for a week. As shown in FIG. 21, high light (600 $\mu E\ m^{-2}\ s^{-1}$) approximately doubled the ethylene production from both strains compared to 50 $\mu E\ m^{-2}\ s^{-1}$, with the peak rate reaching 5700 $\mu L\ L^{-1}\ h^{-1}$ for the strain expressing two copies of efe. The culture growing in high light also reached a higher density than the one grown in low light.

Example 13

Ethylene Production in Sea Water

Figure 24:
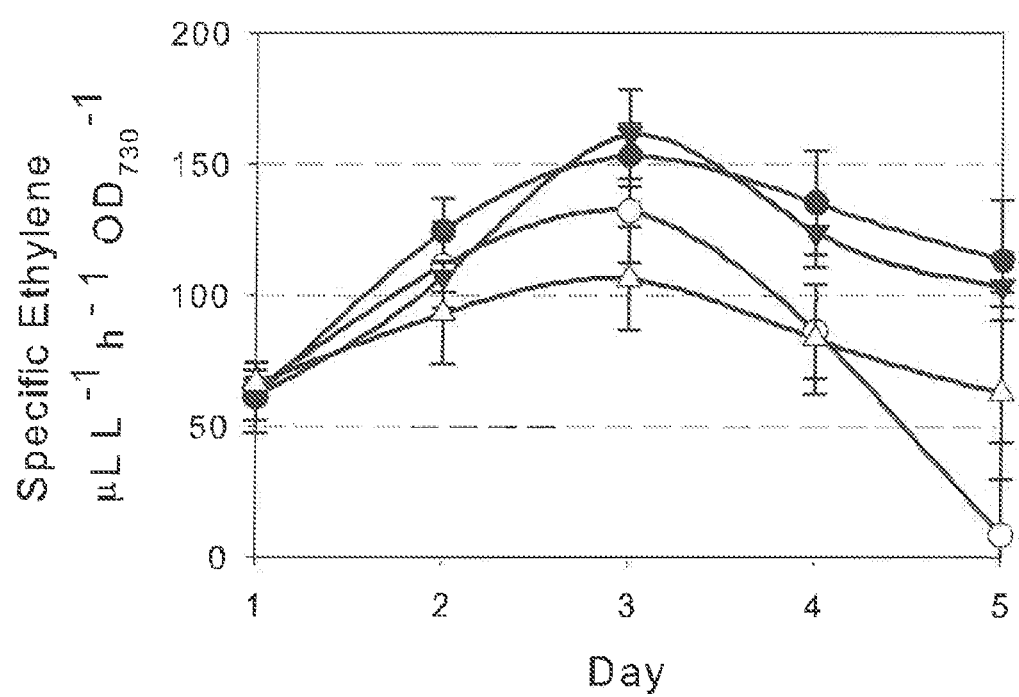
FIG. 24 shows specific ethylene production of a strain harboring a single copy of efe in different types of media. Closed circles—5× BG11; open circle—5× BG11 dissolved in seawater; closed triangle—seawater supplemented with 4 mg/L phosphate and 150 mg/L nitrate; open triangle—sea water (n=3).

Competition for fresh water and arable land is a serious concern for biofuel production. To determine whether sea water could serve as a substitute for 5× BG11, ethylene production in the presence of regular seawater, 5× BG11 media, or 5× BG11 medium made with sea water was examined. Filter sterilized sea-pure (Caribsea) ocean water was used to substitute for BG11 in sea-water experiments. Ethylene production was impaired in sea water; however, seawater supplemented with 4 mg/L phosphate and 150 mg/L nitrate (the same concentrations that are used in 5× BG11) could support growth and ethylene production at rates comparable to those observed with 5× BG11 medium (FIG. 24). Replacing growth medium with supplemented sea water can lower the production cost of ethylene and conserve fresh water for other uses. Furthermore, photosynthetic ethylene production could be located in brackish water bodies, sea bay or coastal areas where it would not compete for arable land and fresh water.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. An isolated nucleic acid molecule encoding a polypeptide that functions as an ethylene-forming enzyme, wherein the nucleic acid molecule has a sequence at least 90% identical to SEQ ID NO:3.

2. The isolated nucleic acid molecule of claim 1, wherein the nucleic acid molecule has a sequence at least 95% identical to SEQ ID NO:3.

3. The isolated nucleic acid molecule of claim 1, wherein the nucleic acid molecule has the sequence of SEQ ID NO:3.

4. The isolated nucleic acid molecule of claim 1, further comprising a promoter operably linked to the nucleic acid molecule.

5. The isolated nucleic acid molecule of claim 4, wherein the promoter is petE or psbA.

6. An expression vector comprising the nucleic acid molecule of claim 1.

7. A host cell comprising the expression vector of claim 6.

8. The host cell of claim 7, wherein the cell is a microbial cell.

9. The host cell of claim 7, wherein the cell is a cyanobacterial cell.

10. The host cell of claim 7, wherein the cell is a *Synechocystis* cell.

11. The host cell of claim 7, wherein the cell is a *Synechocystis* sp. PCC6803 cell.

12. A method for producing ethylene, comprising:
   a) culturing a host cell that expresses a recombinant ethylene-forming enzyme under conditions that allow for ethylene production, wherein the recombinant ethylene-forming enzyme is encoded by a nucleic acid molecule with a sequence at least 90% identical to SEQ ID NO:3; and
   b) isolating ethylene from the culture.

13. The method of claim 12, wherein the cell is a *Synechocystis* cell.

14. The method of claim 12, further comprising a step of replenishing components of a culture medium that are depleted during the culturing step to the cell culture.

15. The method of claim 12, wherein ethylene is produced at a peak production rate of at least 500 nL mL$^{-1}$ hr$^{-1}$.

16. The method of claim 12, wherein the step of culturing comprises providing the cell carbon dioxide and light.

17. The method of claim 16, wherein the light is sunlight.

18. The method of claim 16, wherein the carbon dioxide is atmospheric carbon dioxide.

19. A method for producing ethylene, comprising culturing the host cell of claim 7 under conditions that allow for the production of ethylene by the cell and isolating the ethylene produced by the cell.

* * * * *